(12) United States Patent
Hart et al.

(10) Patent No.: US 11,138,732 B2
(45) Date of Patent: Oct. 5, 2021

(54) ASSESSMENT OF FUNDUS IMAGES

(71) Applicant: Welch Allyn, Inc., Skaneateles Falls, NY (US)

(72) Inventors: Allen R. Hart, Knoxville, TN (US); Hongying Krause, Surrey (GB); Su Wang, Surrey (GB); Ynjiun P. Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 56 days.

(21) Appl. No.: 16/443,234

(22) Filed: Jun. 17, 2019

(65) Prior Publication Data

US 2020/0202529 A1 Jun. 25, 2020

Related U.S. Application Data

(60) Provisional application No. 62/783,689, filed on Dec. 21, 2018.

(51) Int. Cl.
| | |
|---|---|
| *G06K 9/00* | (2006.01) |
| *G06T 7/00* | (2017.01) |
| *G06N 20/00* | (2019.01) |
| *A61B 3/12* | (2006.01) |
| *G06N 3/08* | (2006.01) |

(52) U.S. Cl.
CPC .............. *G06T 7/0014* (2013.01); *A61B 3/12* (2013.01); *G06N 3/08* (2013.01); *G06N 20/00* (2019.01); *G06T 2207/20084* (2013.01); *G06T 2207/30041* (2013.01)

(58) Field of Classification Search
None
See application file for complete search history.

(56) References Cited

U.S. PATENT DOCUMENTS

| | | |
|---|---|---|
| 8,879,813 B1 | 11/2014 | Solanki et al. |
| 9,462,945 B1 | 10/2016 | Barriga et al. |
| 2012/0249956 A1 | 10/2012 | Narashimha-Iyer et al. |
| 2014/0276025 A1* | 9/2014 | Durbin .................... A61B 3/18 600/427 |
| 2015/0223688 A1 | 8/2015 | Wang et al. |
| 2017/0020389 A1 | 1/2017 | Wang et al. |
| 2017/0119241 A1 | 5/2017 | Farchione et al. |
| 2018/0068440 A1 | 3/2018 | Tang et al. |

FOREIGN PATENT DOCUMENTS

| | | |
|---|---|---|
| WO | 2018/049041 A1 | 3/2018 |
| WO | 2018224838 A1 | 12/2018 |

OTHER PUBLICATIONS

U.S. Appl. No. 16/229,939 entitled "Fundus Image Capturing," filed Dec. 21, 2018.
Extended European Search Report for Application No. 19183021.5, dated Jan. 16, 2020.
Pires Dias et al., "Retinal image quality assessment using generic image quality indicators," Information Fusion, vol. 19, pp. 73-90 (Aug. 16, 2012).

\* cited by examiner

*Primary Examiner* — Wei Wen Yang
(74) *Attorney, Agent, or Firm* — Merchant & Gould P.C.

(57) ABSTRACT

An example method for automating a quality assessment of digital fundus image can include: obtaining a digital fundus image file; analyzing a first quality of the digital fundus image file using a model to estimate an optimal time to capture a fundus image; and analyzing a second quality of the digital fundus image file using the model to estimate a disease state.

20 Claims, 24 Drawing Sheets

ASSESSMENT OF FUNDUS IMAGES

RELATED APPLICATION(S)

This patent application is related to U.S. patent application Ser. No. 15/054,558 filed on Feb. 26, 2016, the entirety of which is hereby incorporated by reference.

INTRODUCTION

Diabetic retinopathy and other similar disease states can be diagnosed by studying an image of the retina. Retinal images can be reviewed manually by a clinician. However, manual review is labor-intensive process and subject to error.

For example, people with type 1 or type 2 diabetes can develop eye disease as a result of having diabetes. One of the most common diabetic eye diseases is diabetic retinopathy, which is damage to the blood vessels of the light-sensitive tissue at the back of the eye, known as the retina. Trained medical professionals use cameras during eye examinations for diabetic retinopathy screening. The cameras can produce images of the back of the eye, and trained medical professionals use those images to diagnose and treat diabetic retinopathy.

SUMMARY

An example method for automating a quality assessment of digital fundus image can include: obtaining a digital fundus image file; analyzing a first quality of the digital fundus image file using a model to estimate an optimal time to capture a fundus image; and analyzing a second quality of the digital fundus image file using the model to estimate a disease state.

An example system for automating a quality assessment of digital fundus image can include: a processor; and memory encoding instructions which, when executed by the processor, cause the system to: obtain a digital fundus image file; analyze an optical quality of the digital fundus image file using a neural network to estimate an optimal time to capture a fundus image; and analyze a second quality of the digital fundus image file using the model to estimate a disease state.

DESCRIPTION OF THE FIGURES

The following drawing figures, which form a part of this application, are illustrative of described technology and are not meant to limit the scope of the disclosure in any manner.

DETAILED DESCRIPTION

Figure 1:
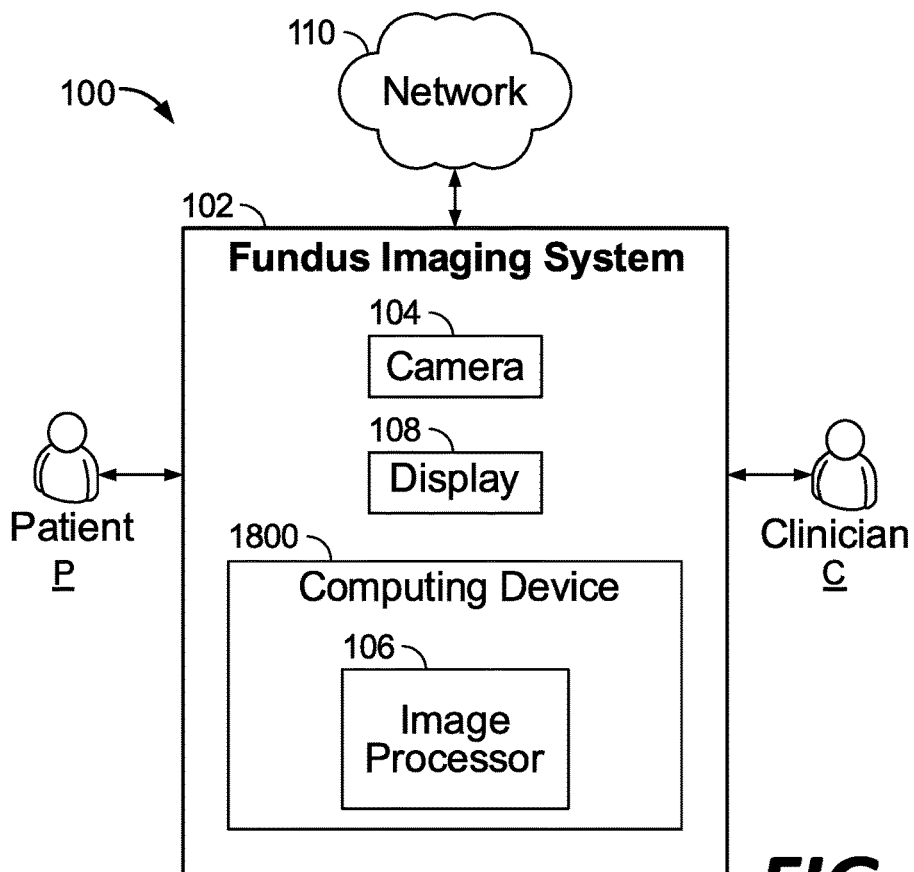
FIG. 1 is an embodiment of an example system for recording and viewing an image of a patient's fundus.

FIG. 1 is a schematic block diagram illustrating an example system 100 for recording and viewing an image of a patient's fundus. In this example, the system 100 includes a patient P, a fundus imaging system 102, a computing device 1800 including an image processor 106, a camera 104 in communication with the computing device 1800, a display 108 in communication with the computing device 1800 and used by clinician C, and a network 110. An embodiment of the example fundus imaging system 102 is shown and described in more detail below with reference to FIG. 4.

The fundus imaging system 102 functions to create a set of digital images of a patient's P eye fundus. As used herein, "fundus" refers to the eye fundus and includes the retina, optic nerve, macula, vitreous, choroid and posterior pole.

In this example, one or more images of the eye are desired. For instance, the patient P is being screened for an eye disease, such as diabetic retinopathy. The fundus imaging system 102 can also be used to provide images of the eye for other purposes, such as to diagnose or monitor the progression of a disease such as diabetic retinopathy.

The fundus imaging system 102 includes a handheld housing that supports the system's components. The housing supports one or two apertures for imaging one or two eyes at a time. In embodiments, the housing supports positional guides for the patient P, such as an optional adjustable chin rest. The positional guide or guides help to align the patient's P eye or eyes with the one or two apertures. In embodiments, the housing supports means for raising and lowering the one or more apertures to align them with the patient's P eye or eyes. Once the patient's P eyes are aligned, the clinician C then initiates the image captures by the fundus imaging system 102.

One technique for fundus imaging requires mydriasis, or the dilation of the patient's pupil, which can be painful and/or inconvenient to the patient P. Example system 100 does not require a mydriatic drug to be administered to the patient P before imaging, although the system 100 can image the fundus if a mydriatic drug has been administered.

The system 100 can be used to assist the clinician C in screening for, monitoring, or diagnosing various eye diseases, such as hypertension, diabetic retinopathy, glaucoma and papilledema. It will be appreciated that the clinician C that operates the fundus imaging system 102 can be different from the clinician C evaluating the resulting image.

In the example embodiment 100, the fundus imaging system 102 includes a camera 104 in communication with an image processor 106. In this embodiment, the camera 104 is a digital camera including a lens, an aperture, and a sensor array. The camera 104 lens is a variable focus lens, such as a lens moved by a step motor, or a fluid lens, also known as a liquid lens in the art. The camera 104 is configured to record images of the fundus one eye at a time. In other embodiments, the camera 104 is configured to record an image of both eyes substantially simultaneously. In those embodiments, the fundus imaging system 102 can include two separate cameras, one for each eye.

In example system 100, the image processor 106 is operatively coupled to the camera 104 and configured to communicate with the network 110 and display 108.

The image processor 106 regulates the operation of the camera 104. Components of an example computing device, including an image processor, are shown in more detail in FIG. 7, which is described further below.

The display 108 is in communication with the image processor 106. In the example embodiment, the housing supports the display 108. In other embodiments, the display connects to the image processor, such as a smart phone, tablet computer, or external monitor. The display 108 functions to reproduce the images produced by the fundus imaging system 102 in a size and format readable by the clinician C. For example, the display 108 can be a liquid crystal display (LCD) and active matrix organic light emitting diode (AMOLED) display. The display can be touch sensitive.

The example fundus imaging system 102 is connected to a network 110. The network 110 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 102 and an external display using one or more wired or wireless protocols, such as Bluetooth, Wi-Fi Direct, radio-frequency identification (RFID), or Zigbee. Other configurations are possible.

Figure 2:
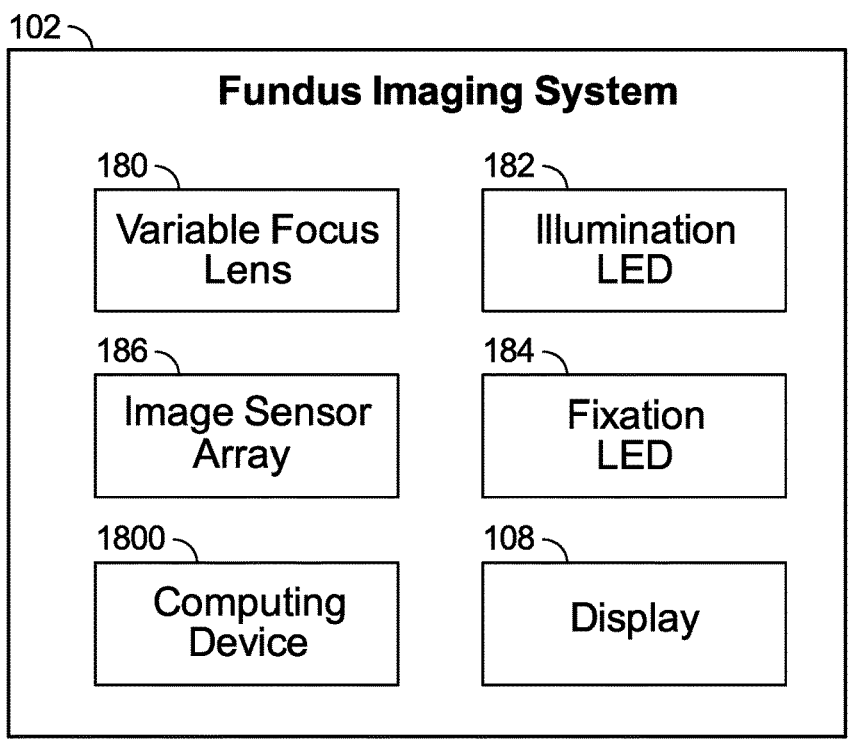
FIG. 2 is an embodiment of an example fundus imaging system.

FIG. 2 illustrates components of an example fundus imaging system 102. The example fundus imaging system 102 includes a variable focus lens 180, an illumination LED 182, an image sensor array 186, a fixation LED 184, a computing device 1800, and a display 108. Each component is in electrical communication with, at least, the computing device 1800. Other embodiments can include more or fewer components.

In one of the embodiments, the variable focus lens 180 is a liquid lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting.

Generally, a liquid lens can focus between about −10 diopters to about +30 diopters. The focus of a liquid lens can be made quickly, even with large changes in focus. For instance, some liquid lenses can autofocus in tens of milliseconds or faster. Liquid lenses can focus from about 10 cm to infinity and can have an effective focal length of about 16 mm or shorter.

In another embodiment of example fundus imaging system 102, the variable focus lens 180 is one or more movable lenses that are controlled by one or more stepping motors, voice coils, ultrasonic motors, piezoelectric actuators, or the like. Additionally, a stepping motor can also move the image sensor array 186 along one, two, and/or free axes. In those embodiments, the variable focus lens 180 and/or the image sensor array 186 are oriented normal to an optical axis of the fundus imaging system 102 and move along at least the optical axis. Additional details are shown and described below with reference to FIG. 4.

The example fundus imaging system 102 also includes an illumination light-emitting diode (LED) 182. The illumination LED 182 can be single color or multi-color. For example, the illumination LED 182 can be a three-channel RGB LED, where each die is capable of independent and tandem operation.

Optionally, the illumination LED 182 is an assembly including one or more visible light LEDs and a near-infrared LED. The optional near-infrared LED can be used in a preview mode, for example, for the clinician C to determine or estimate the patient's P eye focus without illuminating visible light that could cause the pupil to contract or irritate the patient P.

The illumination LED 182 is in electrical communication with the computing device 1800. Thus, the illumination of illumination LED 182 is coordinated with the adjustment of the variable focus lens 180 and image capture. The illumination LED 182 can be overdriven to draw more than the maximum standard current draw rating. In other embodiments, the illumination LED 182 can also include a near-infrared LED. The near-infrared LED is illuminated during a preview mode.

The example fundus imaging system 102 also optionally includes a fixation LED 184. The fixation LED 184 is in communication with the computing device 1800 and produces a light to guide the patient's P eye for alignment. The fixation LED 184 can be a single color or multicolor LED. For example, the fixation LED 184 can produce a beam of green light that appears as a green dot when the patient P looks into the fundus imaging system 102. Other colors and designs, such as a cross, "x" and circle are possible.

The example fundus imaging system 102 also includes an image sensor array 186 that receives and processes light reflected by the patient's fundus. The image sensor array 186 is, for example, a complementary metal-oxide semiconductor (CMOS) sensor array, also known as an active pixel sensor (APS), or a charge coupled device (CCD) sensor.

The image sensor array 186 has a plurality of rows of pixels and a plurality of columns of pixels. In some embodiments, the image sensor array has about 1280 by 1024 pixels, about 640 by 480 pixels, about 1500 by 1152 pixels, about 2048 by 1536 pixels, or about 2560 by 1920 pixels.

In some embodiments, the pixel size in the image sensor array 186 is from about four micrometers by about four micrometers; from about two micrometers by about two micrometers; from about six micrometers by about six micrometers; or from about one micrometer by about one micrometer.

The example image sensor array 186 includes photodiodes that have a light-receiving surface and have substantially uniform length and width. During exposure, the photodiodes convert the incident light to a charge. The image sensor array 186 can be operated as a global reset, that is, substantially all of the photodiodes are exposed simultaneously and for substantially identical lengths of time.

The example fundus imaging system 102 also includes a display 108, discussed in more detail above with reference to FIG. 1. Additionally, the example fundus imaging system 102 includes a computing device 1800, discussed in more detail below with reference to FIG. 7.

Figure 3:
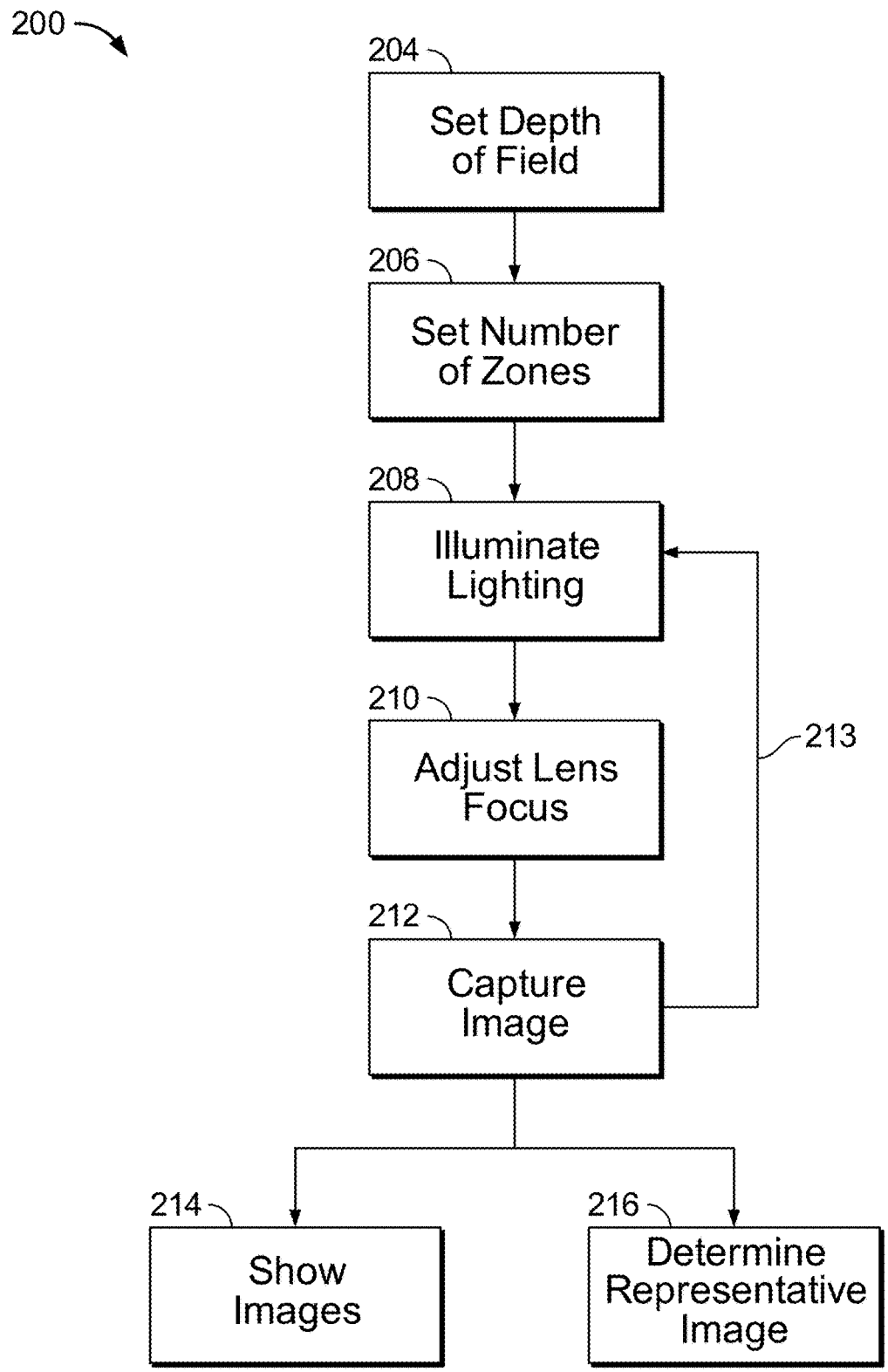
FIG. 3 is an embodiment of an example method for imaging a patient's fundus using a fundus imaging system.

FIG. 3 is an embodiment of a method 200 for imaging a patient's fundus using a fundus imaging system. In the embodiment shown, the lighting is optimally dimmed prior to execution, although lowering the lighting is optional. The embodiment shown includes a set depth of field operation 204, a set number of zones operation 206, an illuminate lighting operation 208, an adjust lens focus operation 210, a capture image operation 212, repeat operation(s) 213, a show images operation 214 and a determine representative image operation 216. Other embodiments can include more or fewer steps.

The embodiment of method 200 begins with setting a depth of field operation 204. In embodiments, the variable focus lens 180 is capable of focusing from about −20 diopters to about +20 diopters. Set depth of field operation 204 defines the lower and upper bounds in terms of diopters. For example, the depth of field range could be set to about −10 to +10 diopters; about −5 to about +5 diopters; about −10 to about +20 diopters; about −5 to about +20 diopters; about −20 to about +0 diopters; or about −5 to about +5 diopters. Other settings are possible. The depth of field can be preprogrammed by the manufacturer. Alternatively, the end user, such as the clinician C, can set the depth of field.

As shown in FIG. 3, the next operation in embodiment of method 200 is setting the number of zones operation 206. However, zones operation 206 can occur before or concurrent with field operation 204. In zones operation 206, the depth of field is divided into equal parts, where each part is called a zone. In other embodiments, the zones are not all equal. The number of zones is equal to the number of images captured in capture image operation 212.

For example, when the depth of field is from −10 to +10 diopters, the focus of the variable focus lens can be changed by 4 diopters before each image capture. Thus, in this example, images would be captured at −10, −6, −2, +2, +6 and +10 diopters. Or, images could be captured at −8, −4, 0, +4 and +8 diopters, thereby capturing an image in zones −10 to −6 diopters, −6 to −2 diopters, −2 to +2 diopters, +2 to +6 diopters and +6 to +10 diopters, respectively. In that instance, the depth of focus is about +/−2 diopters. Of course, the number of zones and the depth of field can vary, resulting in different ranges of depth of field image capture.

In embodiments, both depth of field and number of zones are predetermined. For example, −10 D to +10 D and 5 zones. Both can be changed by a user.

After the depth of field and number of zones are set, the next operation in embodiment of method 200 is the image capture process, which includes illuminate lighting operation 208, adjust lens focus operation 210 and capture image operation 212. As shown in FIG. 3, the lighting component is illuminated (lighting operation 208) before the lens focus is adjusted (lens focus operation 210). However, lens focus operation 210 can occur before or concurrent with lighting operation 208.

The illumination LED 182 is illuminated in lighting operation 208. The illumination LED 182 can remain illuminated throughout the duration of each image capture. Alternatively, the illumination LED 182 can be turned on and off for each image capture. In embodiments, the illumination LED 182 only turns on for the same period of time as the image sensor array 186 exposure time period.

Optionally, lighting operation 208 can additionally include illuminating a near-infrared LED. The clinician C can use the illumination of the near-infrared LED as a way to preview the position of the patient's P pupil.

The focus of variable focus lens 180 is adjusted in lens focus operation 210. Autofocusing is not used in embodiment of method 200. That is, the diopter setting is provided to the lens without regard to the quality of the focus of the image. Indeed, traditional autofocusing fails in the low-lighting non-mydriatic image capturing environment. The embodiment of method 200 results in a plurality of images at least one of which, or a combination of which, yields an in-focus view of the patient's P fundus.

Additionally, the lack of autofocusing enables the fundus imaging system 102 to rapidly capture multiple images in capture image operation 212 at different diopter ranges. That is, variable focus lens 180 can be set to a particular diopter range and an image captured without the system verifying that the particular focus level will produce an in-focus image, as is found in autofocusing systems. Because the system does not attempt to autofocus, and the focus of the variable focus lens 180 can be altered in roughly tens of milliseconds, images can be captured throughout the depth of field in well under a second, in embodiments. Thus, in the embodiment of method 200, the fundus imaging system 102 can capture images of the entire depth of field before the patient's P eye can react to the illuminated light. Without being bound to a particular theory, depending on the patient P, the eye might react to the light from illumination LED 182 in about 150 milliseconds.

The image sensor array 186 captures an image of the fundus in capture image operation 212. As discussed above, the embodiment of method 200 includes multiple image captures of the same fundus at different diopter foci. The example fundus imaging system 102 uses a global reset or global shutter array, although other types of shutter arrays, such as a rolling shutter, can be used. The entire image capture method 200 can also be triggered by passive eye tracking and automatically capture, for example, 5 frames of images. An embodiment of example method for passive eye tracking is shown and described in more detail with reference to FIG. 5, below.

After the fundus imaging system 102 captures an image of the fundus, the embodiment of method 200 returns in loop 213 to either the illuminate lighting operation 208 or the adjust lens focus operation 210. That is, operations 208, 210 and 212 are repeated until an image is captured in each of the preset zones from zones operation 206. It is noted that the image capture does not need to be sequential through the depth of field. Additionally, each of the images does not need to be captured in a single loop; a patient could have one or more fundus images captured and then one or more after a pause or break.

After an image is captured in each of the zones (capture image operation 212) in embodiment of method 200, either the images are displayed in show images operation 214 or a representative image is determined in operation 216 and then the image is displayed. Show images operation 214 can include showing all images simultaneously or sequentially on display 108. A user interface shown on display 108 can then enable the clinician C or other reviewing medical professional to select or identify the best or a representative image of the patient's P fundus.

In addition to, or in place of, show images operation 214, the computing device can determine a representative fundus image in operation 216. Operation 216 can also produce a single image by compiling aspects of one or more of the images captured. This can be accomplished by, for example, using a wavelet feature reconstruction method to select, interpolate, and/or synthesize the most representative frequency or location components.

The fundus imaging system 102 can also produce a three-dimensional image of the fundus by compiling the multiple captured images. Because the images are taken at different focus ranges of the fundus, the compilation of the pictures can contain three-dimensional information about the fundus.

In turn, the image or images from operation 214 or 216 can be sent to a patient's electronic medical record or to a different medical professional via network 110.

Figure 4:
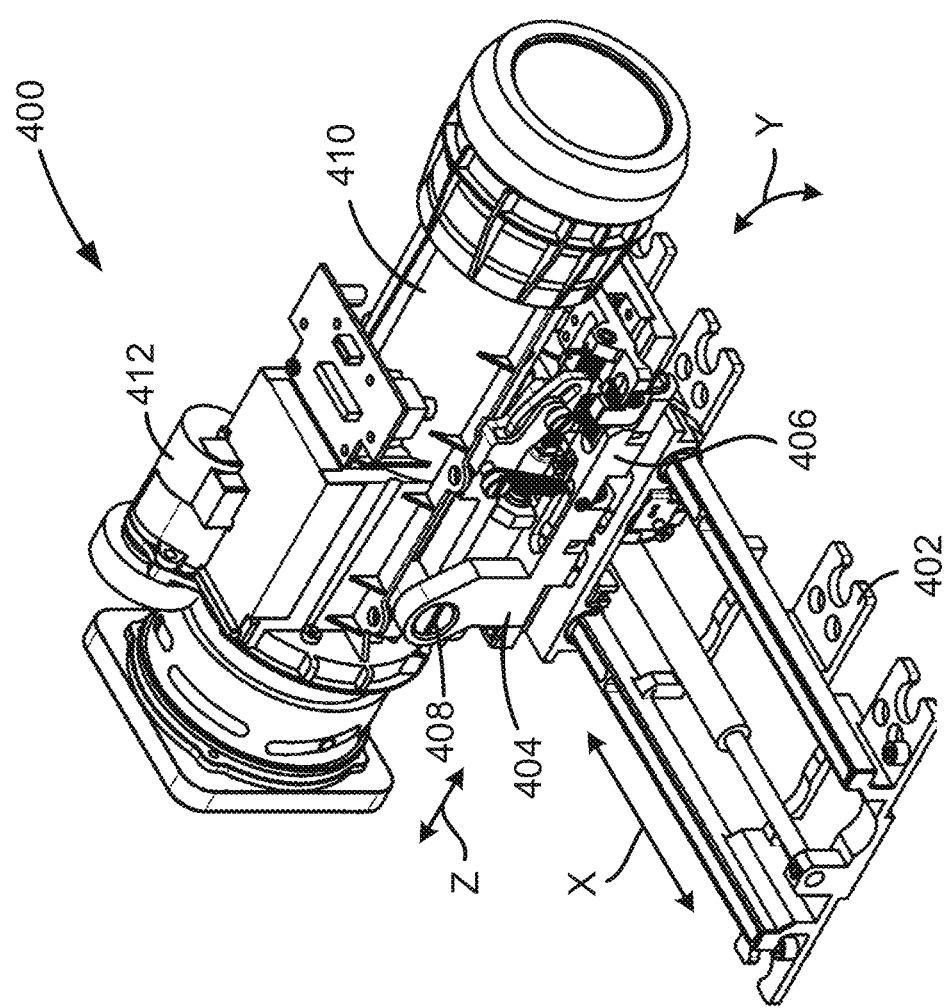
FIG. 4 is an embodiment of an example fundus imaging system.

FIG. 4 illustrates internal components of an embodiment of a fundus imaging system 400. The embodiment 400 includes an optical lens module 410 with an auto-focus motor 412 mounted on multiple bases that allow for travel in multiple axes, along with a pitch.

An x-base 402 allows for travel of the optical lens module 410 in an x direction. This can include travel up to 78 mm in the x direction. An z-base 404 allows for travel of the optical lens module 410 in a z direction. This can include travel up to 30 mm in the z direction.

In addition, the fundus imaging system 400 optionally includes a y-pitch base 406 that allows the optical lens module 410 to be pitched in the y direction about a bearing 408. In this example, the pitch allows for 10.55 mm of travel, which results in +4.08 degrees to −2.88 degrees of y pitch.

The fundus imaging system 400 is similar to the system described in U.S. patent application Ser. No. 16/229,939 filed on Dec. 21, 2018 and/or U.S. patent application Ser. No. 15/054,558 filed on Feb. 26, 2016, the entireties of which are hereby incorporated by reference.

Figure 5:
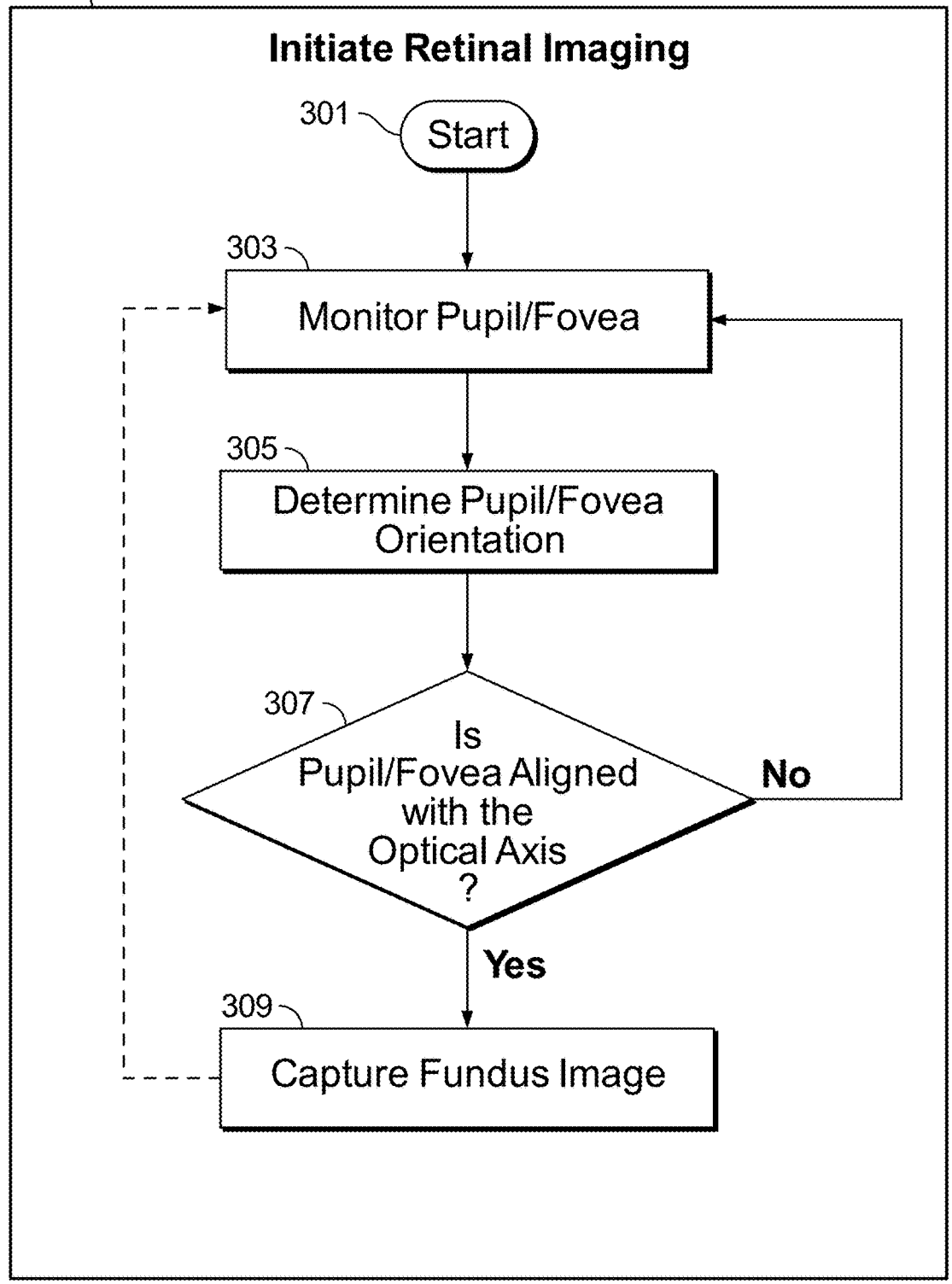
FIG. 5 illustrates an example method of initiating a fundus imaging using passive eye tracking.

FIG. 5 illustrates an alternate embodiment of initiate retinal imaging step 306 using passive eye tracking. The initiate retinal imaging step 306 operates to image the fundus of the patient P using passive eye tracking. In the initiate retinal imaging step 306, the fundus imaging system 102 monitors the pupil/fovea orientation of the patient P. Although the initiate retinal imaging step 306 is described with respect to fundus imaging system 102, the initiate retinal imaging step 306 may be performed using a wearable or nonwearable fundus imaging system, such as a handheld digital fundus imaging system.

Initially, at step 303, the pupil or fovea or both of the patient P are monitored. The fundus imaging system 102 captures images in a first image capture mode. In the first image capture mode, the fundus imaging system 102 captures images at a higher frame rate. In some embodiments, in the first image capture mode, the fundus imaging system 102 captures images with infra-red illumination and at lower resolutions. In some embodiments, the infra-red illumination is created by the illumination LED 182 operating to generate and direct light of a lower intensity towards the subject. The first image capture mode may minimize discomfort to the patient P, allow the patient P to relax, and allow for a larger pupil size without dilation (non-mydriatic).

Next, at step 305, the computing device 1800 processes at least a portion of the images captured by the fundus imaging system 102. The computing device 1800 processes the images to identify the location of the pupil or fovea or both of the patient P. Using the location of the pupil or fovea or both in one of the images, a vector corresponding to the pupil/fovea orientation is calculated. In some embodiments, the pupil/fovea orientation is approximated based on the distance between the pupil and fovea in the image. In other embodiments, the pupil/fovea orientation is calculated by approximating the position of the fovea relative to the pupil in three dimensions using estimates of the distance to the pupil and the distance between the pupil and the fovea. In other embodiments, the pupil/fovea orientation is approximated from the position of the pupil alone. In yet other embodiments, other methods of approximating the pupil/fovea orientation are used.

Next, at step 307, the pupil/fovea orientation is compared to the optical axis of the fundus imaging system 102. If the pupil/fovea orientation is substantially aligned with the optical axis of the fundus imaging system 102, the process proceeds to step 309 to capture a fundus image. If not, the process returns to step 303 to continue to monitor the pupil or fovea. In some embodiments, the pupil/fovea orientation is substantially aligned with the optical axis when the angle between them is less than two to fifteen degrees.

Next, at step 309, fundus images are captured by triggering the embodiment of example thru focusing image capturing method 200. In embodiments, five images are captured at step 309. In some embodiments, the fundus image is captured in a second image capture mode. In some embodiments, in the second image capture mode, the fundus imaging system 102 captures images with visible illumination and at higher resolutions. In some embodiments, the visible illumination is created by the illumination LED 182 operating to generate and direct light of a higher intensity towards the subject. In other embodiments, the higher illumination is created by an external light source or ambient light. The second image capture mode may facilitate capturing a clear, well-illuminated, and detailed fundus image.

Figure 6:
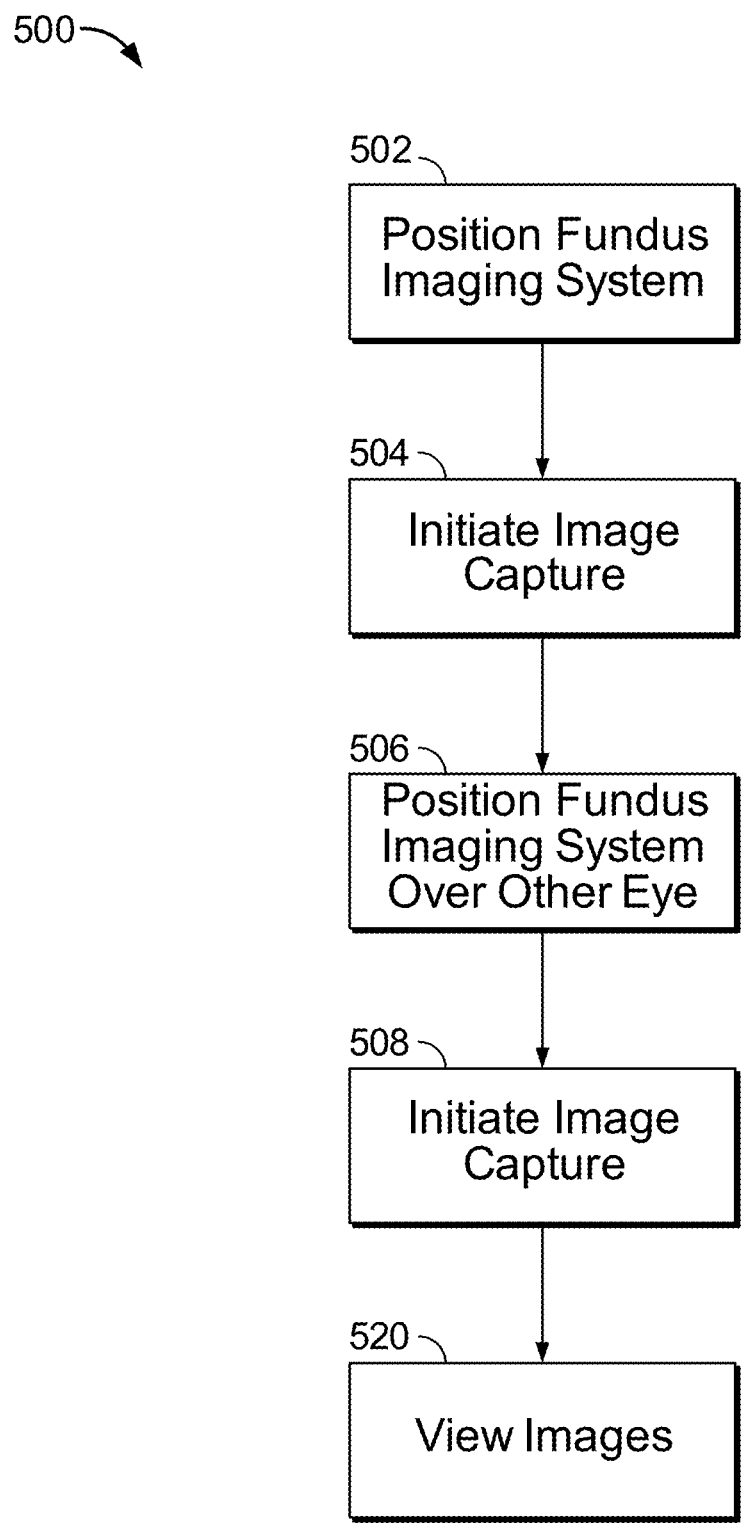
FIG. 6 is an embodiment of an example use of a fundus imaging system.

In some embodiments, after step 309, the initiate retinal imaging step 306 returns to step 303 to continue to monitor the pupil/fovea orientation. The initiate retinal imaging step 306 may continue to collect fundus images indefinitely or until a specified number of images have been collected. Further information regarding passive eye tracking can be found in U.S. patent application Ser. No. 14/177,594 filed on Feb. 11, 2014, titled Ophthalmoscope Device, which is hereby incorporated by reference in its entirety FIG. 6 is an embodiment of example use 500 of fundus imaging system 102. In the embodiment of example use 500, a clinician positions the fundus imaging system (operation 502), initiates image capture (operation 504), positions the fundus imaging system over the other eye (operation 506), initiates image capture (operation 508), and views images (operation 520). Although the example use 500 is conducted without first administering mydriatic pharmaceuticals, the example use 500 can also be performed for a patient who has taken a pupil-dilating compound. The embodiment of example use 500 can also include lowering the lighting. The embodiment of example use 500 is conducted using the same or similar components as those described above with reference to FIGS. 1-3. Other embodiments can include more or fewer operations.

The embodiment of example use 500 begins by positioning the fundus imaging system (operation 502). In embodiments, the clinician first initiates an image capture sequence via a button on the housing or a graphical user interface shown by the display. The graphical user interface can instruct the clinician to position the fundus imaging system over a particular eye of the patient. Alternatively, the clinician can use the graphical user interface to indicate which eye fundus is being imaged first.

In operation 502, the clinician positions the fundus imaging system near the patient's eye socket. The clinician positions the aperture of the system flush against the patient's eye socket such that the aperture, or a soft material eye cup extending from the aperture, seals out most of the ambient light. Of course, the example use 500 does not require positioning the aperture flush against the patient's eye socket.

When the fundus imaging system is in position, the system captures more than one image of the fundus in operation 504. As discussed above, the system does not require the clinician to manually focus the lens. Additionally, the system does not attempt to autofocus on the fundus. Rather, the clinician simply initiates the image capture, via a button or the GUI, and the fundus imaging system controls when to capture the images and the focus of the variable focus lens. Also, as discussed above at least with reference to FIG. 5, the system can initiate image capture using passive eye tracking.

The patient may require the fundus imaging system to be moved away from the eye socket during image capture operation 504. The clinician can re-initiate the image capture sequence of the same eye using the button or the GUI on the display.

After capturing an image in each of the specified zones, the fundus imaging system notifies the clinician that the housing should be positioned over the other eye (operation 506). The notification can be audible, such as a beep, and/or the display can show a notification. In embodiments, the system is configured to capture a set of images of only one eye, wherein the example method 500 proceeds to view images operation 520 after image capture operation 504.

Similar to operation 502, the clinician then positions the fundus imaging system near or flush with the patient's other eye socket in operation 506. Again, when the system is in place, an image is captured in every zone in operation 508.

After images have been captured of the fundus in each pre-set zone, the clinician can view the resulting images in operation 520. As noted above with reference to FIG. 3, the images can be post-processed before the clinician views the images to select or synthesize a representative image. Additionally, the fundus images can be sent to a remote location for viewing by a different medical professional.

Figure 7:
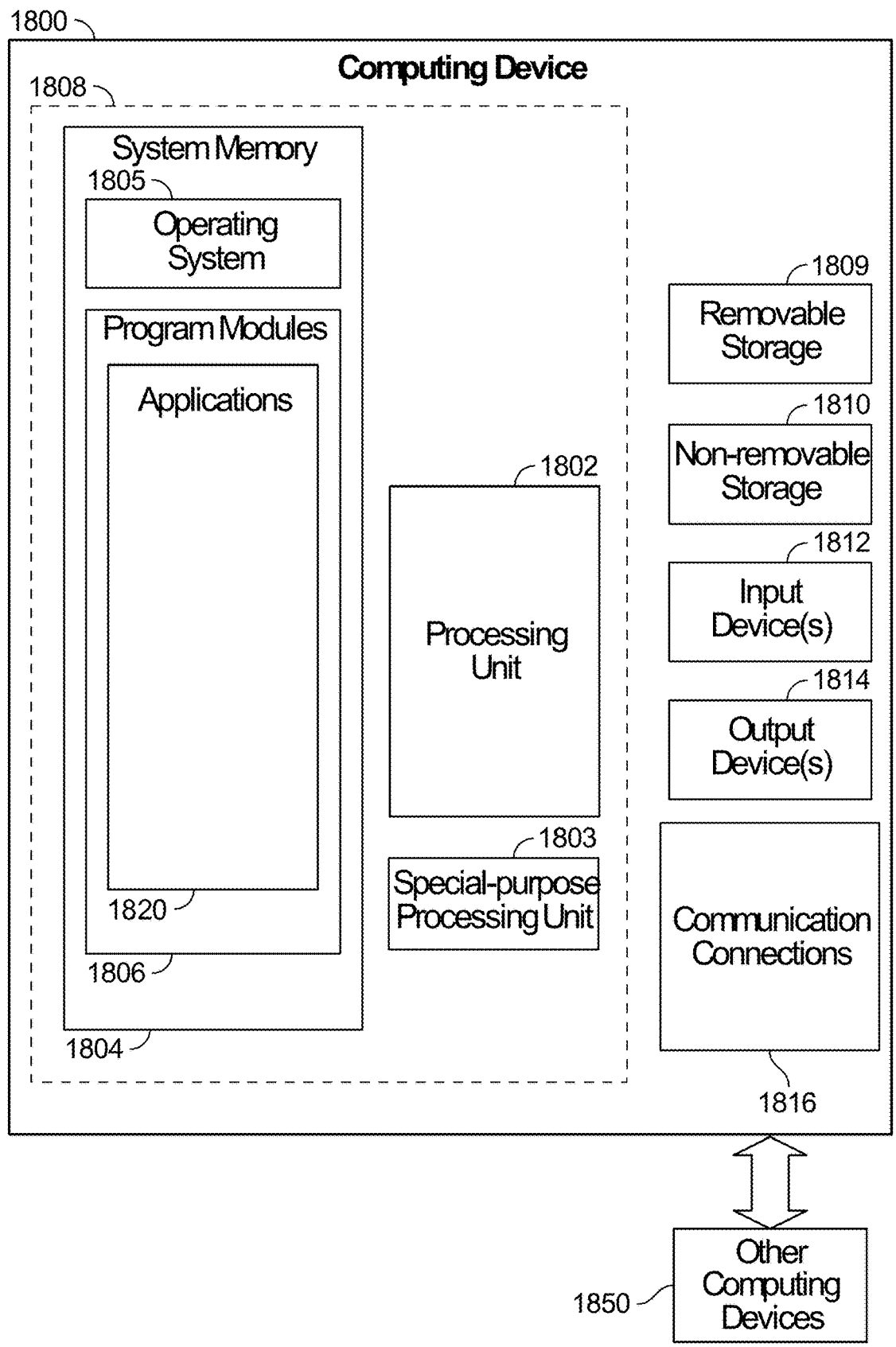
FIG. 7 is an example computing device used within the fundus imaging system.
Figure 8:
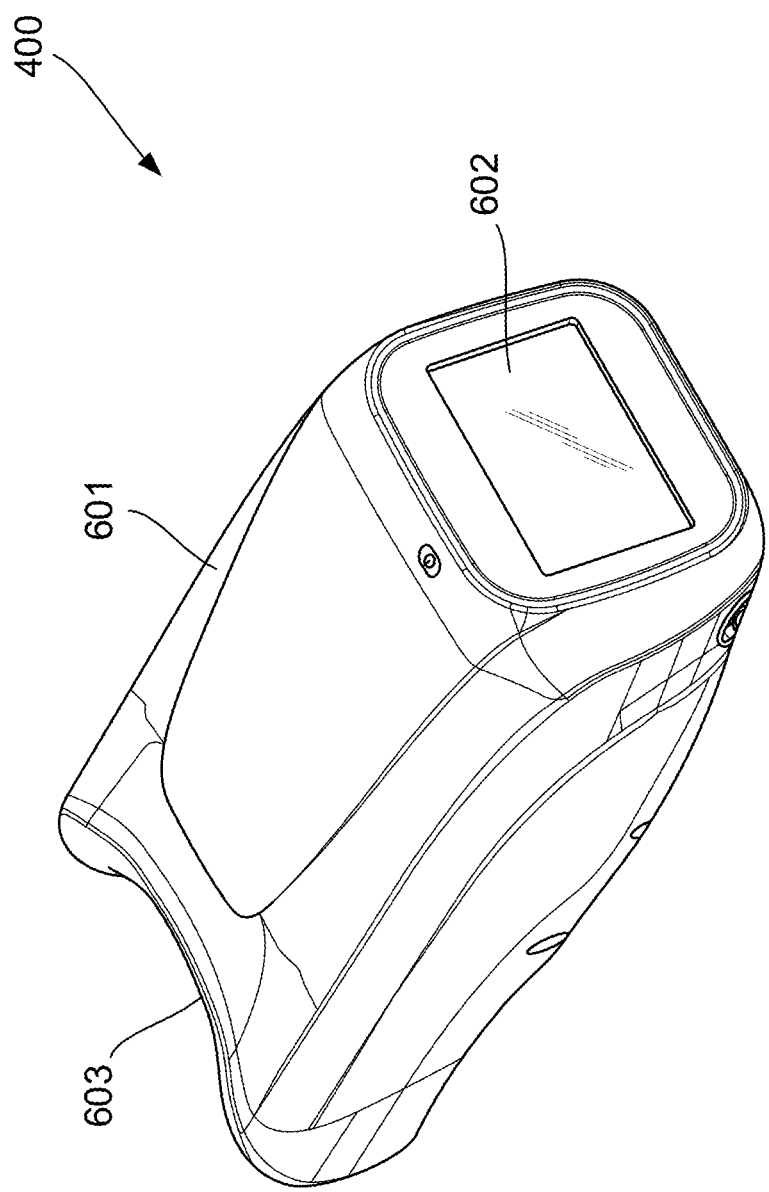
FIG. 8 is another embodiment of an example fundus imaging system.
Figure 9:
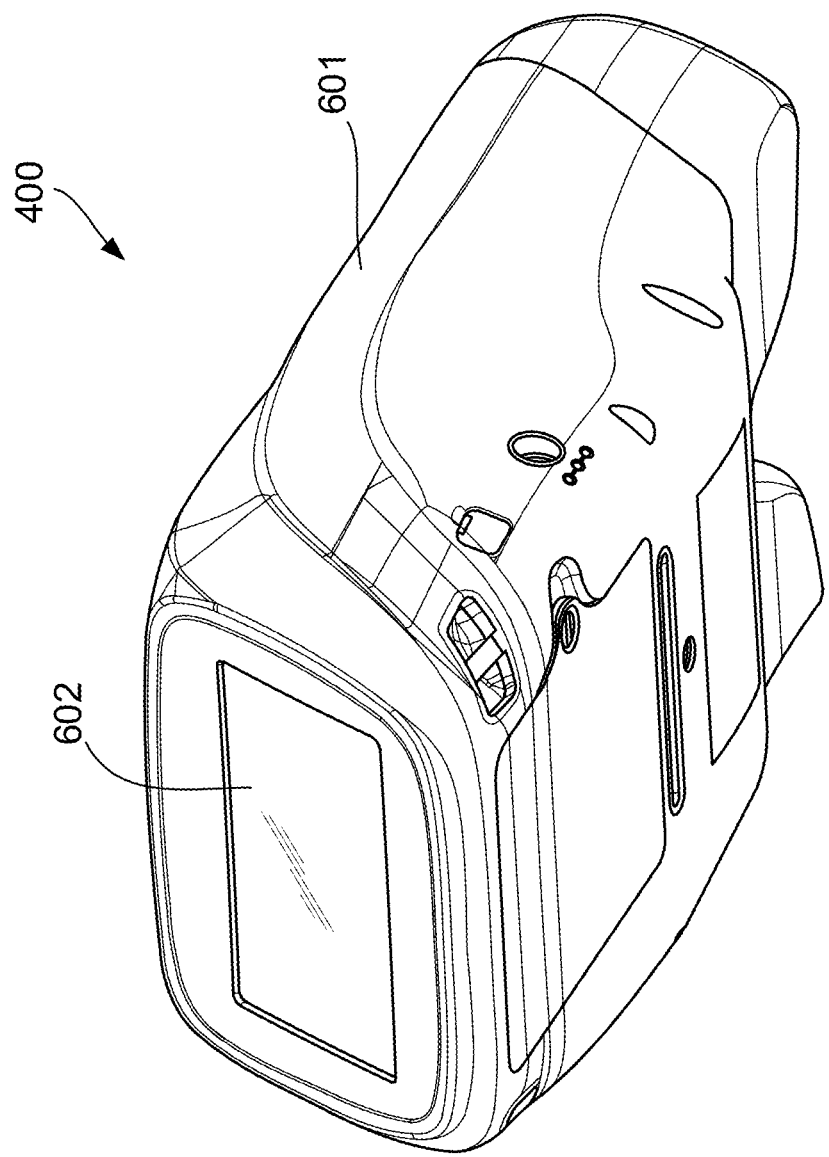
FIG. 9 is another view of the fundus imaging system of FIG. 8.
Figure 10:
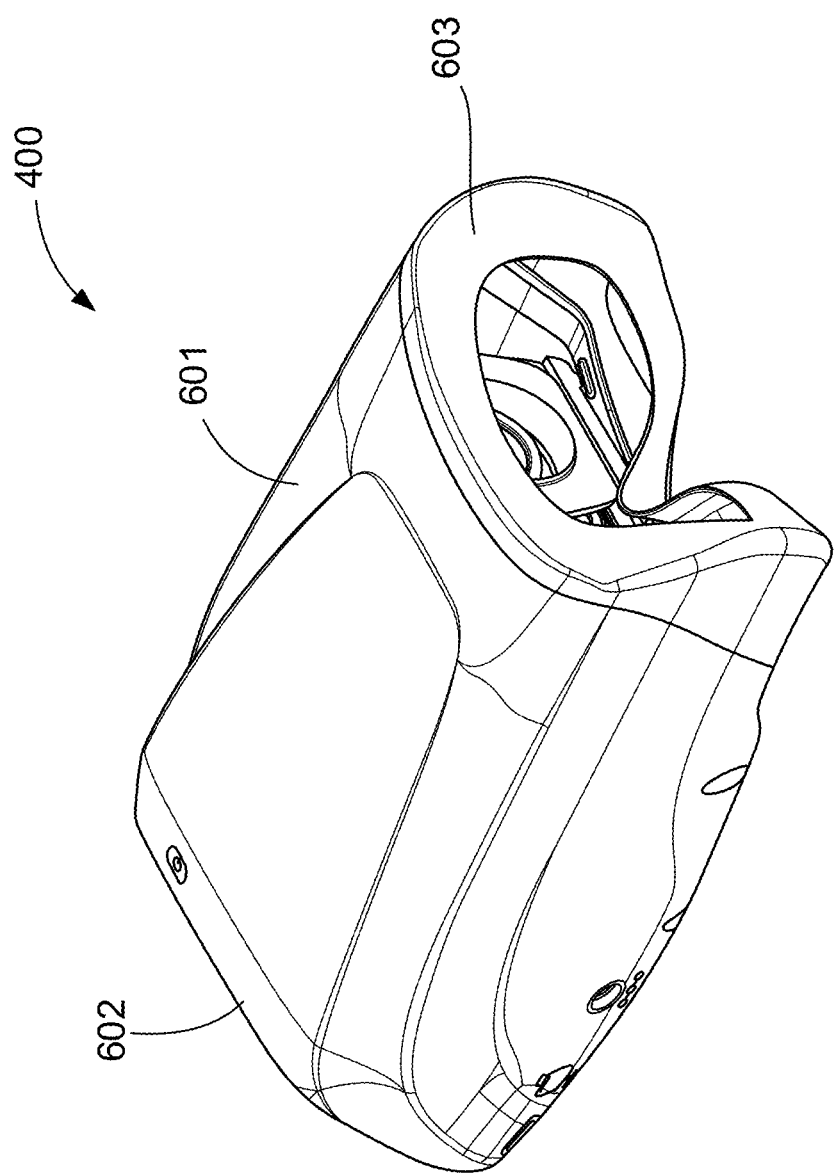
FIG. 10 is another view of the fundus imaging system of FIG. 8.
Figure 11:
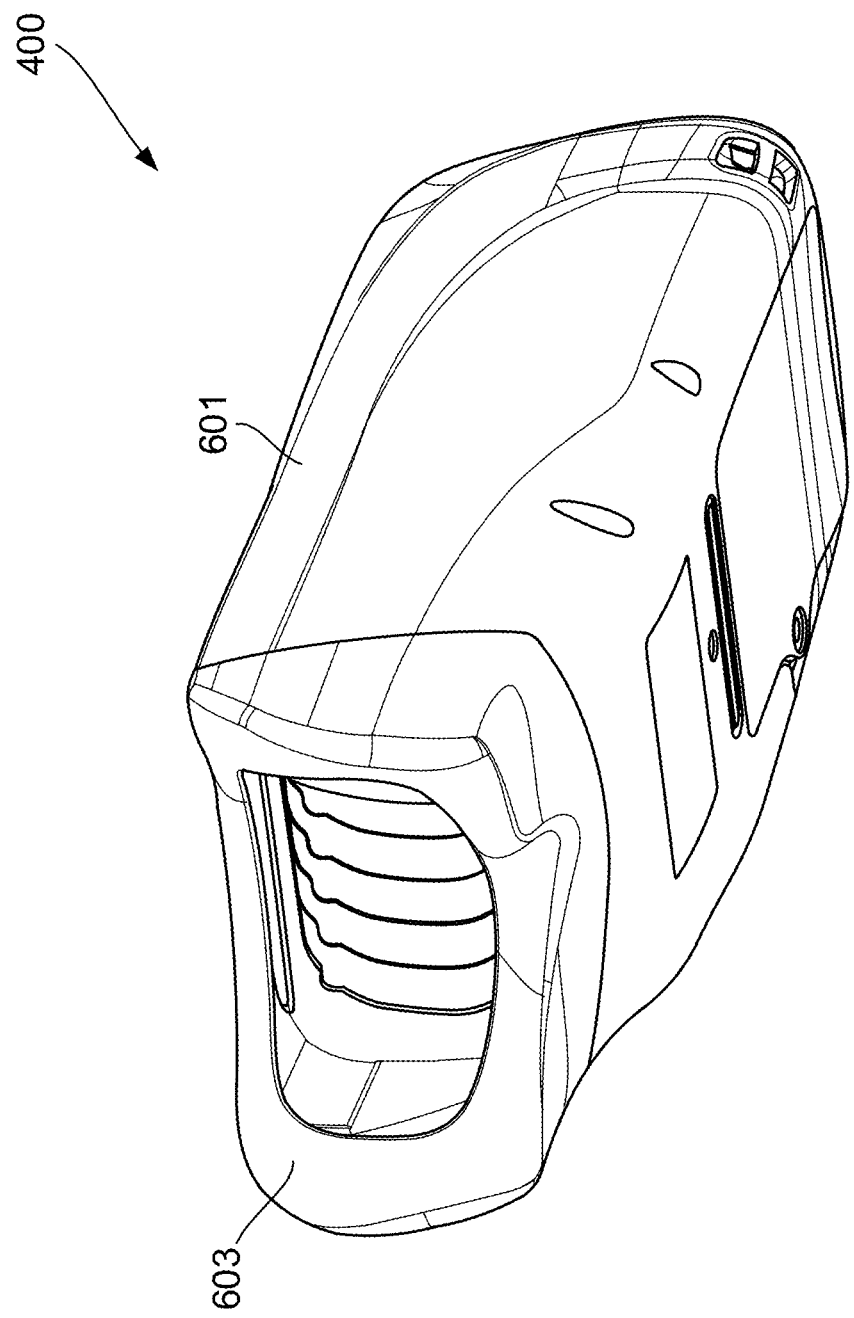
FIG. 11 is another view of the fundus imaging system of FIG. 8.
Figure 12:
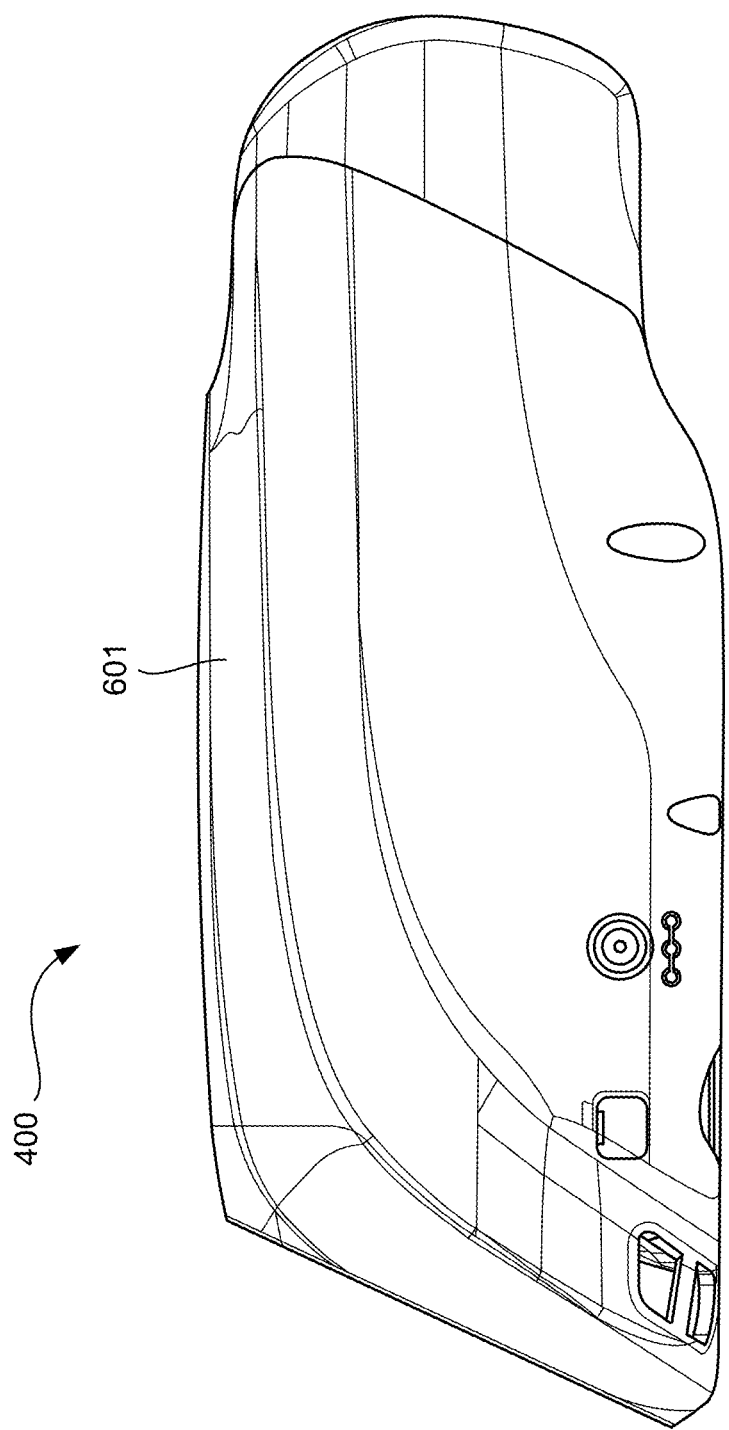
FIG. 12 is another view of the fundus imaging system of FIG. 8.
Figure 13:
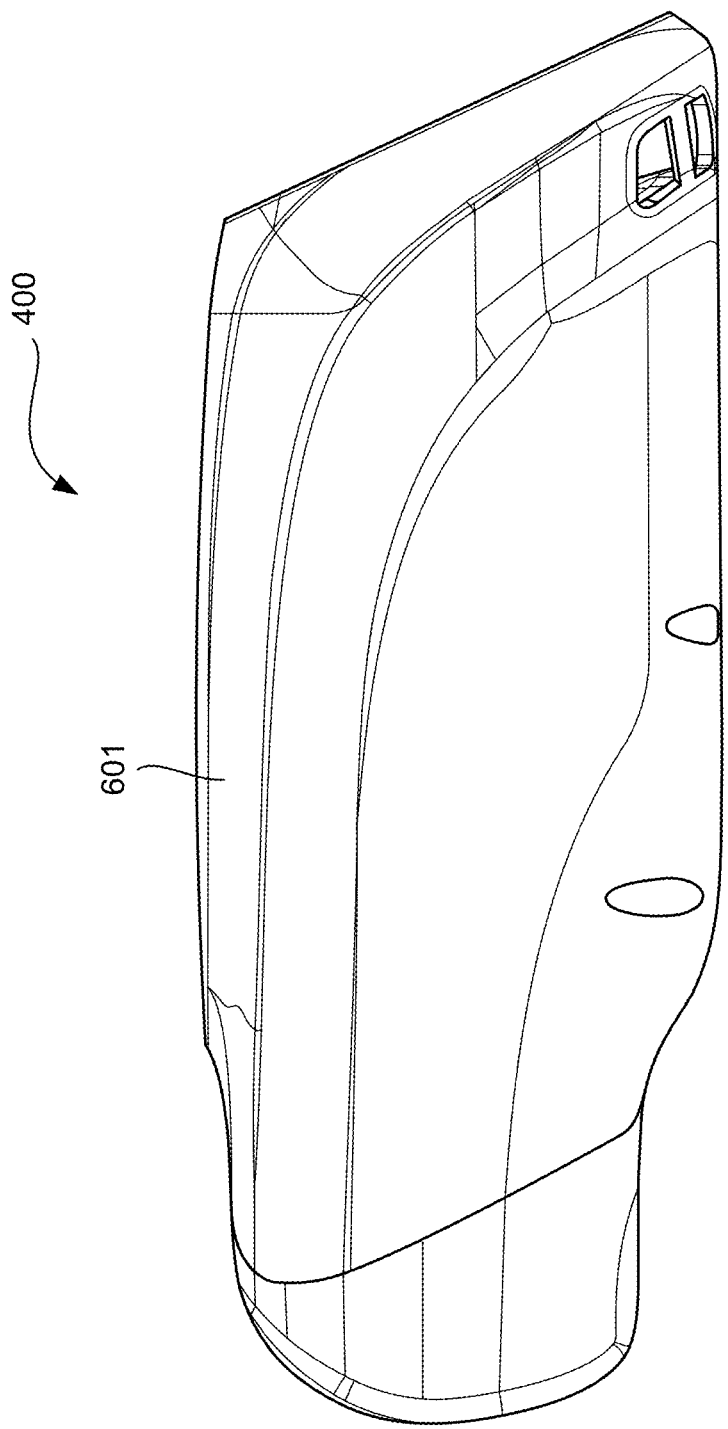
FIG. 13 is another view of the fundus imaging system of FIG. 8.
Figure 14:
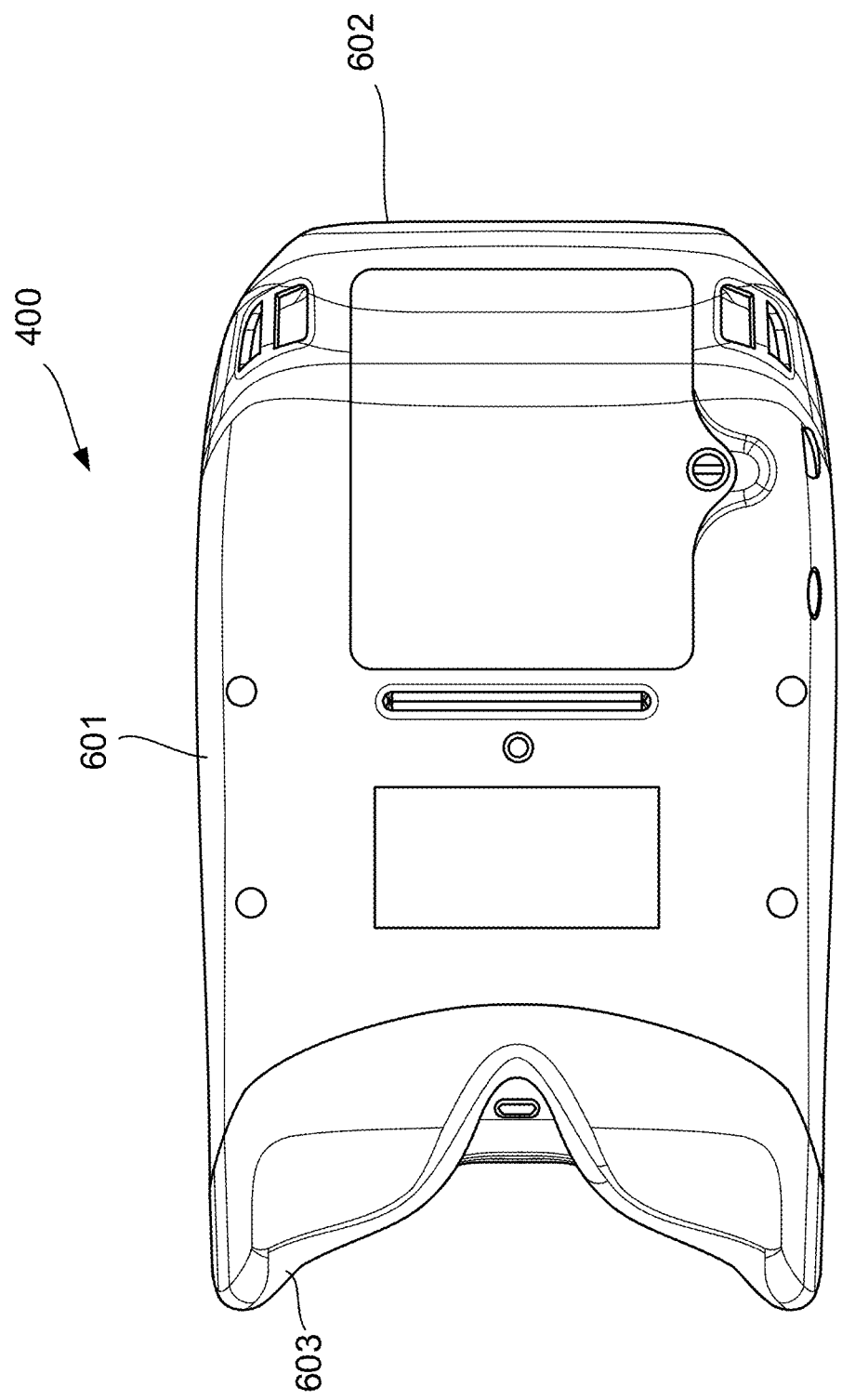
FIG. 14 is another view of the fundus imaging system of FIG. 8.
Figure 15:
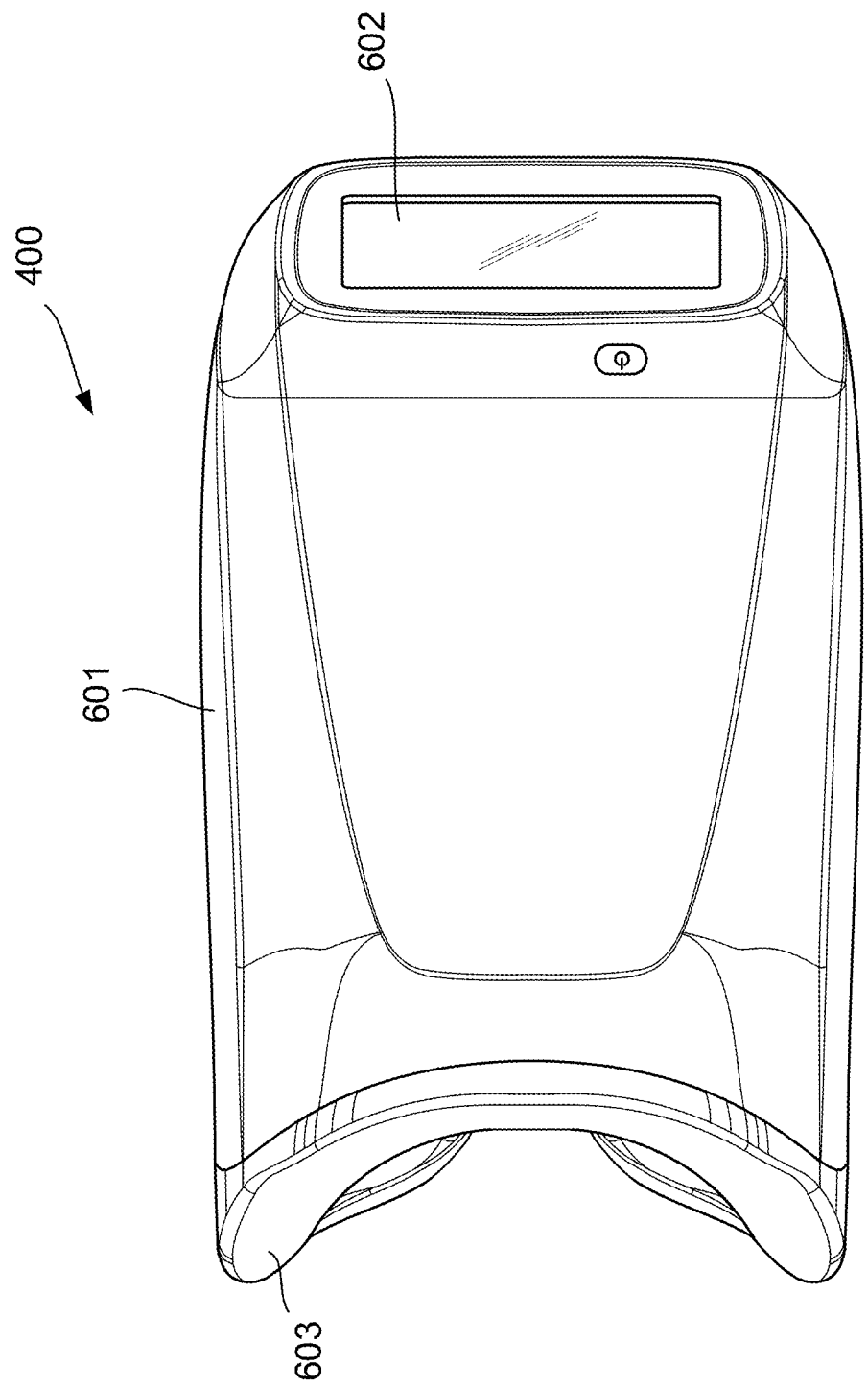
FIG. 15 is another view of the fundus imaging system of FIG. 8.
Figure 16:
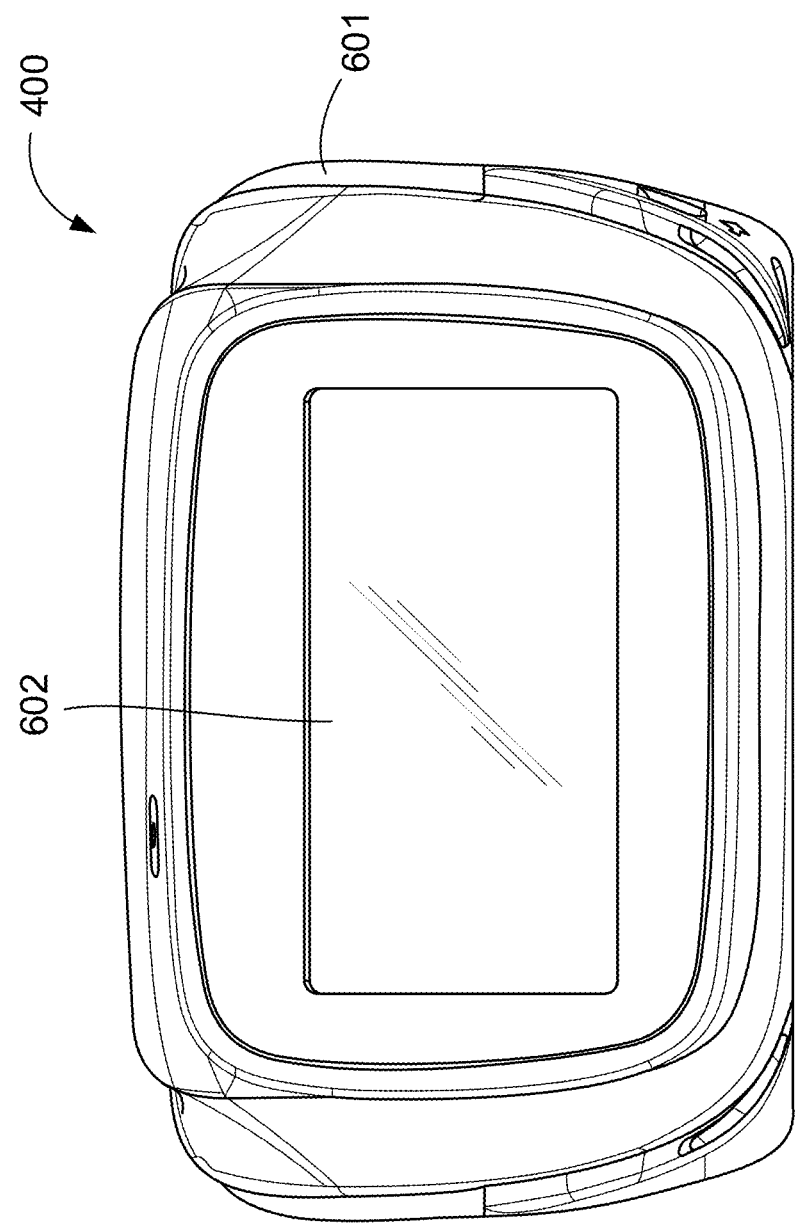
FIG. 16 is another view of the fundus imaging system of FIG. 8.
Figure 17:
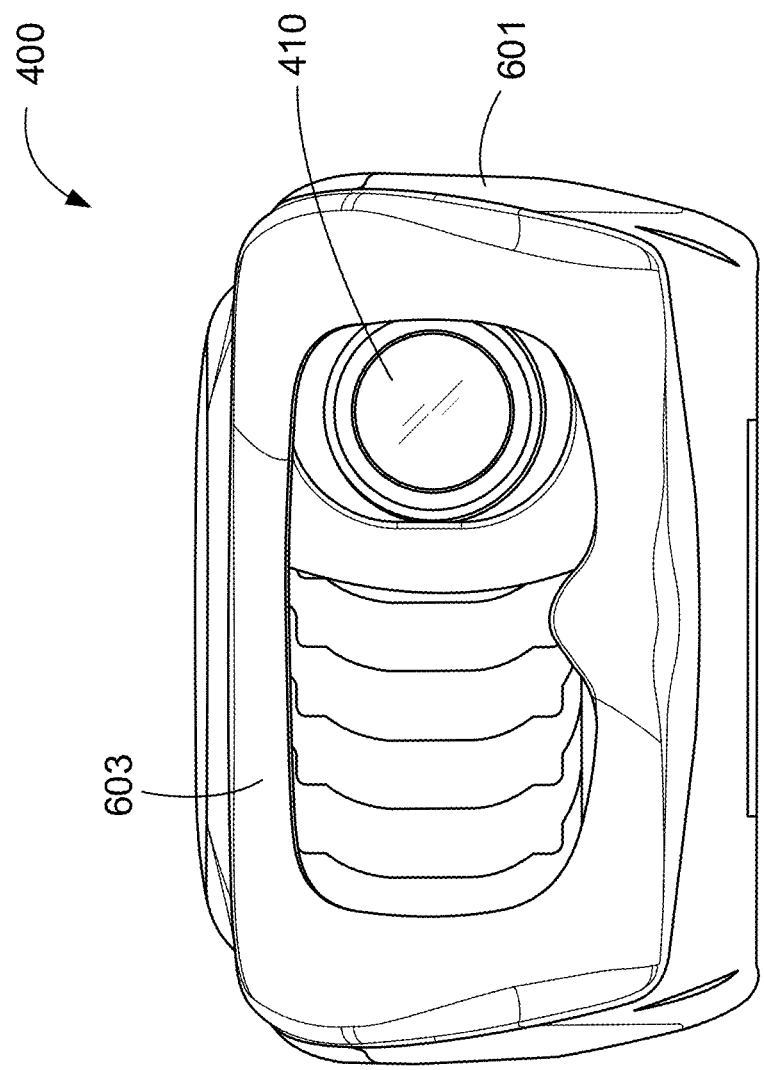
FIG. 17 is another view of the fundus imaging system of FIG. 8.

FIG. 7 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 7 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated in FIG. 7 by a removable storage device 1809 and a non-removable storage device 1810.

As stated above, a number of program modules and data files may be stored in the system memory 1804. While executing on the at least one processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 7 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812 such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

Referring now to FIGS. 8-17, the fundus imaging system 400 is shown. The fundus imaging system 400 includes a housing 601 that supports a display 602 at a first end and an opposite end 603 configured to engage an eye of the patient. As described herein, the fundus imaging system 600 can be used to implement one or more of the described methods for imaging of the fundus.

The housing 601 of example fundus imaging system 400 is sized to be hand held. The display 602 can display images of the eye and controls for capturing those images. The display 602 can, in some instances, be a touchscreen. In embodiments, the housing 601 additionally supports one or more user input buttons near display 602. The user input button can initiate the image capture sequence, at least a portion of which is shown and discussed with reference to FIG. 3, above. Thus, the fundus imaging system 400 is capable of being configured such that the clinician C does not need to adjust the lens focus.

Referring now to FIGS. 18-25, another example system 1000 is shown. In this example, the system 1000 is configured to automate the capture and assessment of fundus imaging using a neural network. Although the example illustrated is an image acquisition system, alternative embodiments are possible. For example, the embodiments described herein can be used with alternative systems that perform image acquisition and analysis.

Figure 18:
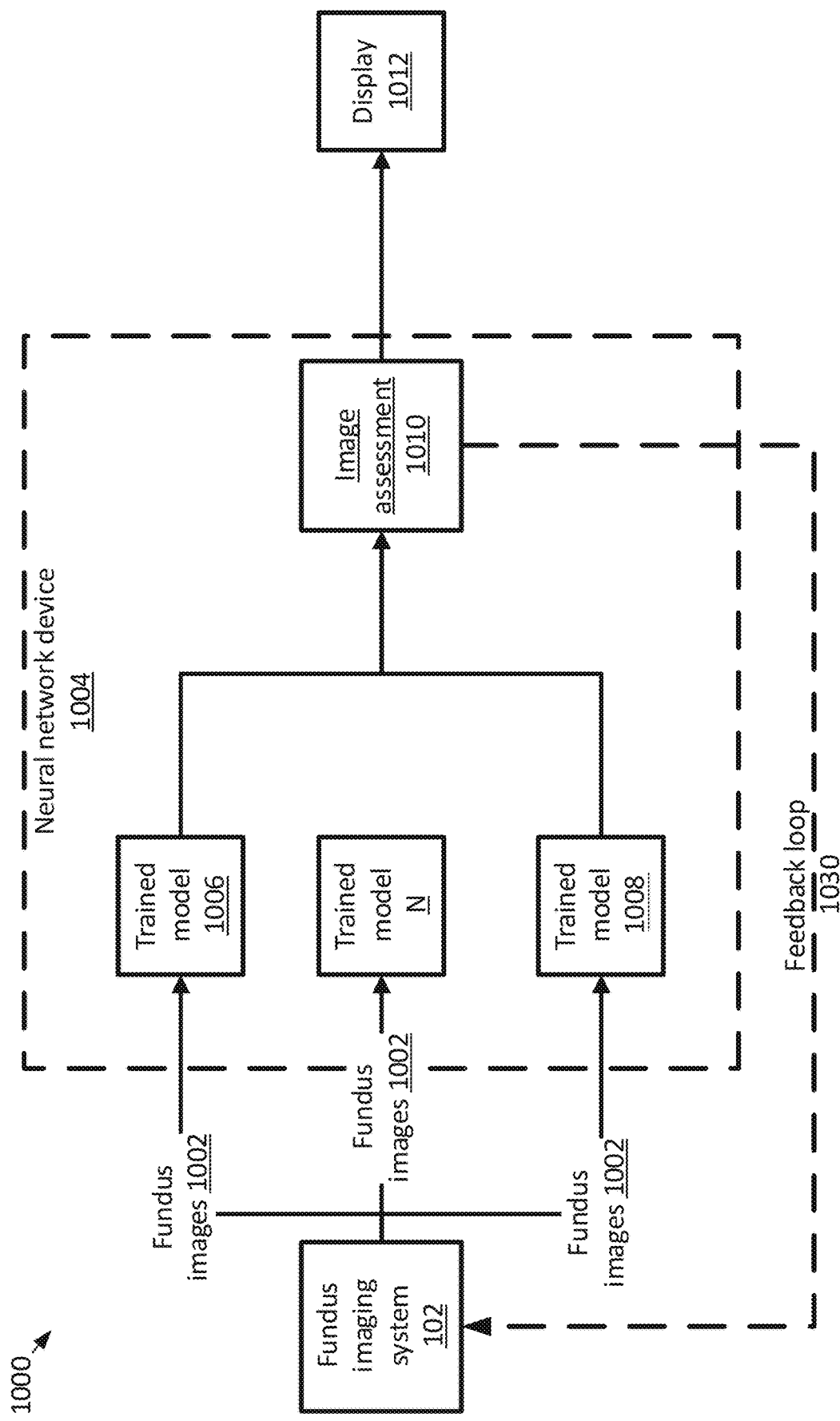
FIG. 18 is an example system for assessing a quality of a fundus image.

Referring specifically to FIG. 18, the system 1000 comprises the fundus imaging system 102 and a neural network device 1004. The fundus imaging system 102 is used, as described above, to capture one or more fundus images 1002. These fundus images are feed into the neural network device 1004 for assessment by one or more trained models 1006, 1008, N.

In this example, the trained models 1006, 1008, N can be one or more convolutional neural networks (CNNs) that are implemented in software or in hardware. When a software implementation is used, the neural network device 1004 may comprise one or more processing units comprising one or more processors, and memory in the form of a suitable computer-readable storage medium. The memory can be arranged to store computer program instructions which, when executed by the processing unit, perform the functions of the neural network device 1004. Other similar types of networks can also be used.

As shown in FIG. 18, the neural network device 1004 is provided with an input retinal image including one or more fundus images 1002 captured by the fundus imaging system 102. In the present embodiment, the neural network device 1004 is configured to receive an input image of size 512×512 pixels, but in other embodiments images of different sizes could be used.

The trained models 1006, 1008 of the neural network device 1004 are programmed to automate the assessment of the images using the image assessment module 1010. In one assessment, the fundus images 1002 are analyzed to provide an objective quality assessment during image acquisition, to guide in the capture of optimal images for various clinical examination purposes. In another assessment, the fundus images 1002 are analyzed to provide an objective quality assessment during image analysis, to guide in the diagnosis of diseases using the fundus images.

The output of the image assessment module 1010 can be displayed by the display 1012. For example, the output can be displayed to the caregiver C to aide in automated image acquisition and/or diagnosis of disease, as described further below.

The assessment of the fundus images 1002 can be measured against a combination of criteria. This criteria can include, without limitation: (1) overall optical quality of the whole images; (2) optical quality in the area of optic disc; (3) optical quality in the area of macula; (4) vessel visibility or vessel count in specific regions; and (5) field position including: (i) macula centered image, and (ii) optic disc centered image. The image assessment can be conducted according to one or more standards, such as the definition of acceptable image quality according to the National Screening Programme for Diabetic Retinopathy. In this example, Version 3.0 dated May 9, 2006 of the standard from the Grading and Quality Assurance Subcommittee is used. In this standard, the following image quality guidelines are defined:

- GOOD Macular image—center of fovea≤1 disk diameter from center of image & vessels clearly visible within 1 disk diameter of center of fovea & vessels visible across>90% of image
- GOOD Disc image—center of disc≤1 disk diameter from center of image & fine vessels clearly visible on surface of disc & vessels visible across>90% of image
- ADEQUATE Macular image—center of fovea>2 disk diameter from edge of image & vessels visible within 1 disk diameter of center of fovea
- ADEQUATE Disc image—complete optic disc>2 disk diameter from edge of image & fine vessels visible on surface of disc (in some unusual cases (particularly in patients with a large disc), an image may fall within both good and adequate categories above—in such cases, the image should be classified as good)
- INADEQUATE (ungradable) —failure to meet definition of adequate above UNLESS referable diabetic retinopathy (R2, R3, M1, unstable treated proliferative diabetic retinopathy) visible anywhere in the eye.

While the neural network is depicted outside of the fundus imaging system 102, in alternative embodiments, the neural network can be embedded in the fundus imaging system 102. For example, the neural network can be an embedded software module or firmware module or hardware module positioned in the fundus imaging system 102. Other configurations are possible.

Figure 19:
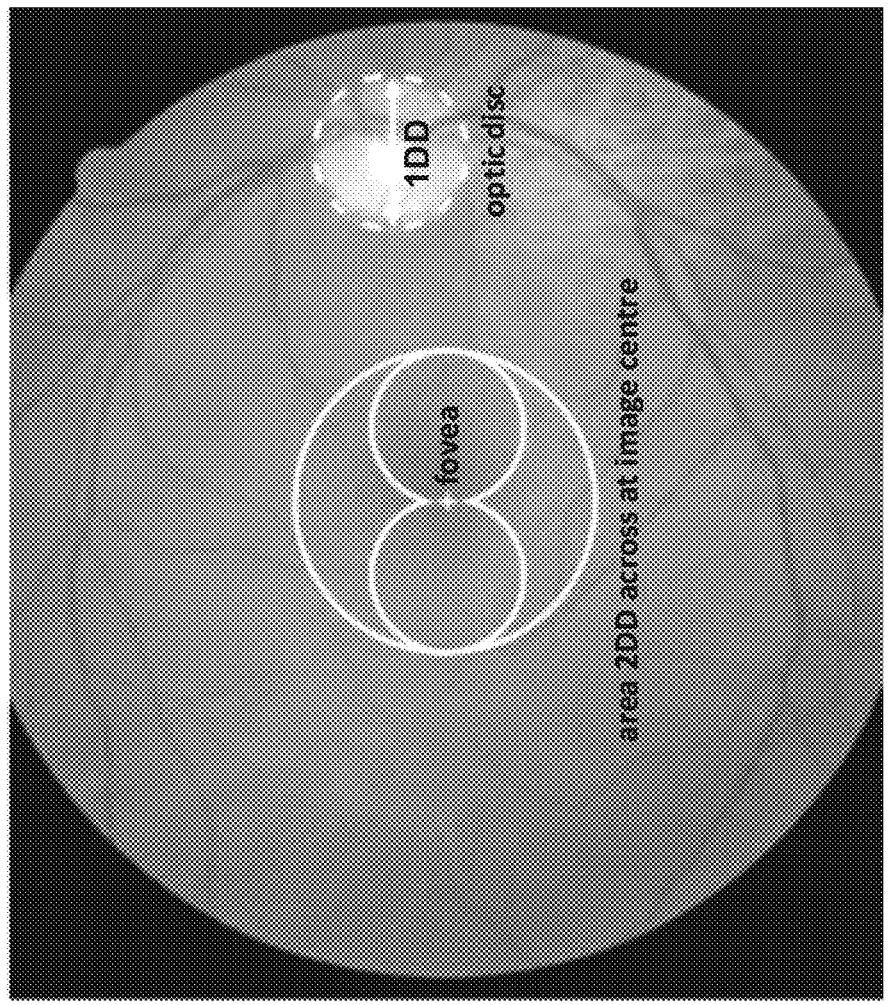
FIG. 19 is an example fundus image having a perfectly-aligned macular view of the right eye.

FIG. 19 illustrates a fundus image 1020 having a perfectly-aligned macular view of the right eye. The fovea lies at the center of the image and is marked by a '+' symbol. (Image is from Definition of acceptable image quality, Version 3.0, Agreed by the Grading and Quality Assurance Subcommittee, 9 May 2006.)

Figure 20:
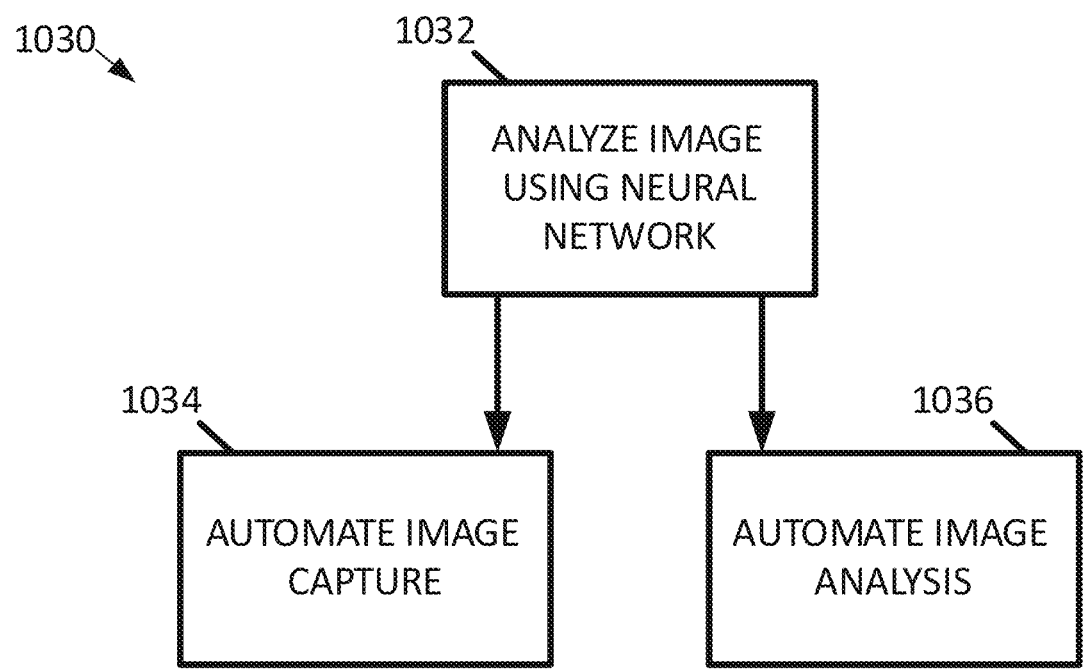
FIG. 20 is an example method for assessing a fundus image to automate capture of an image and/or to automate image analysis.

Referring now to FIG. 20, an example method 1030 as implemented by the system 1000 is provided. In this example, an obtained fundus image is analyzed by the neural network 1004 at operation 1032. This analysis can be used to: at operation 1034, automated image acquisition; and/or at operation 1036, automate diagnosis of disease state(s).

For example, at operation 1034, the analysis of the neural network 1004 can be used (e.g., through a feedback loop 1030 shown in the system 1000) to automate the capture of images by the fundus imaging system 102. For example, one or more of the operations of a method 1050 (described in reference to FIG. 21 below) can be used to analyze a current image as being captured by the fundus imaging system 102 to determine when to automatically capture one or more fundus images for analysis. For example, the fundus imaging system 102 can have an integrated neural network component that allows for the automated capture of an optimal picture at the right time (e.g., when the pupil is large enough), with functions of automated alignments of macula, or OD, or with the previous baseline images.

In addition or alternatively, at operation 1036, a captured fundus image from the fundus imaging system 102 is used to automate the assessment of one or more disease states, as describe further in reference to the method 1050 below.

Figure 21:
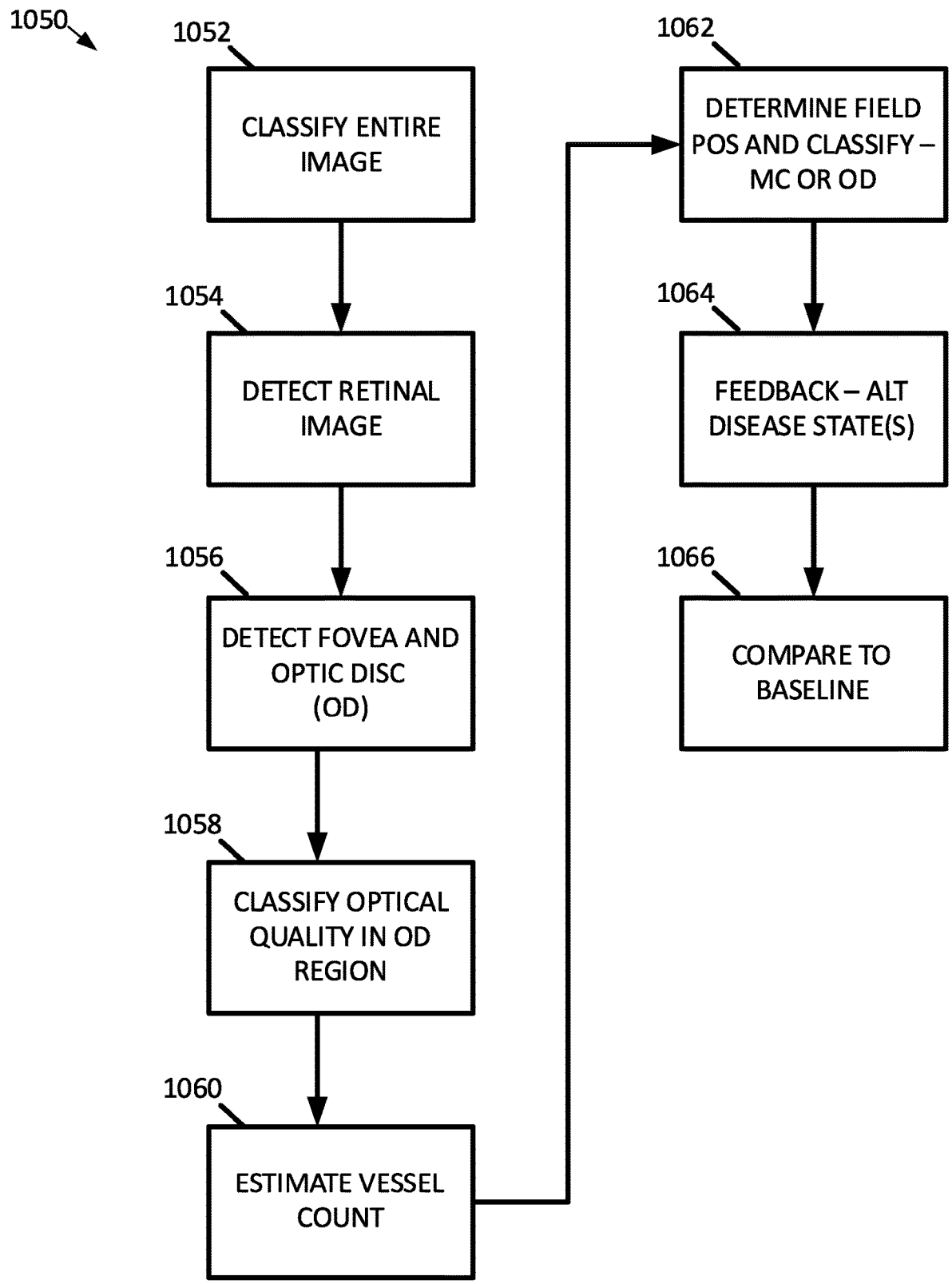
FIG. 21 is an example method for automating the assessment of a fundus image.

Referring now to FIG. 21, the example method 1050 as implemented by the system 1000 is provided. In this example, the method 1050 performs automated image assessment using the neural network device 1004. The results of this assessment can be used, for example, to aide in automated image acquisition and/or diagnosis of disease.

At operation 1052 of the method 1050, the entire fundus image is classified. For instance, the fundus image can be rated as "readable" or "unreadable" by the neural network device 1004. This classification can be accomplished by training the models 1006, 1008, N using a large corpus of images (e.g., 10,000 or more images) that have been labeled by human reviewers as "readable" or "unreadable". The training can be carried out either using customized CNN or through "transfer learning"—i.e., to train the initial CNN using large dataset for general classification such as diabetic retinopathy grading. The trained weights can then be used as a base for further training on quality assessment outputs. The trained models 1006, 1008, N can thereupon predict an image as being "readable" or "unreadable" based upon this training.

In addition, each "readable" image can be rated as "Excellent", "Good", or "Fair". Each "unreadable" image can similarly be rated as "Poor" or "Unacceptable", and further information such as "Not centered", "Cannot grade—obscured areas", or "Cannot grade—poor photo quality" can be provided by the neural network device 1004.

Images that are identified as "unreadable" can be discarded or sent for manual review by a human. If an image is identified as "unreadable", it can be further examined automatically or manually to determine if the image manifests any referable disease, including referable diabetic retinopathy or other diseases. This is because some pathological conditions prevent the light coming through into the retina or have an unusual presentation that makes the image appear to be "unreadable". The pathology may be visible in some part of the image while the rest of the image is unreadable.

If the image is identified as "readable", control is passed to operation 1054, and a determination is made as to whether or not the image is a fundus image.

Specifically, this can be done through the use of the neural network device 1004 that is trained to classify images as "retina" and "non-retina". This classification can be done through a CNN where there are two classes of training data: one is pure retina images; and the other can be any kind of images other than retina images. This can be implemented through a customized CNN, or other established algorithms such as Inception modules or Residual Learning, or other classification algorithms. The non-retina data can be those from ImageNet or from any collection of non-retina images. "Non-retina" classified images are discarded or sent for manual processing.

If the image is identified as a "retina" image, control is instead passed to operation 1056, and the neural network device 1004 is used to detect the fovea and optic disc (OD) of the fundus image. This is accomplished by using the trained models 1006, 1008, N to first detect all vessel pixels. In this example, a U-Net architecture (e.g., a convolutional network for biomedical image segmentation) is used for training the trained models 1006, 1008, N. The major vessels can be then detected to estimate a position of the OD and macula. Trained classifiers for detecting macula and OD can then be applied to locate the precise position. Bother macula and OD classifiers can be trained through a U-net or CNNs or other types of deep or shallow learning algorithms. This process involves preparation of a set of suitable training data for OD and macula.

Figure 22:
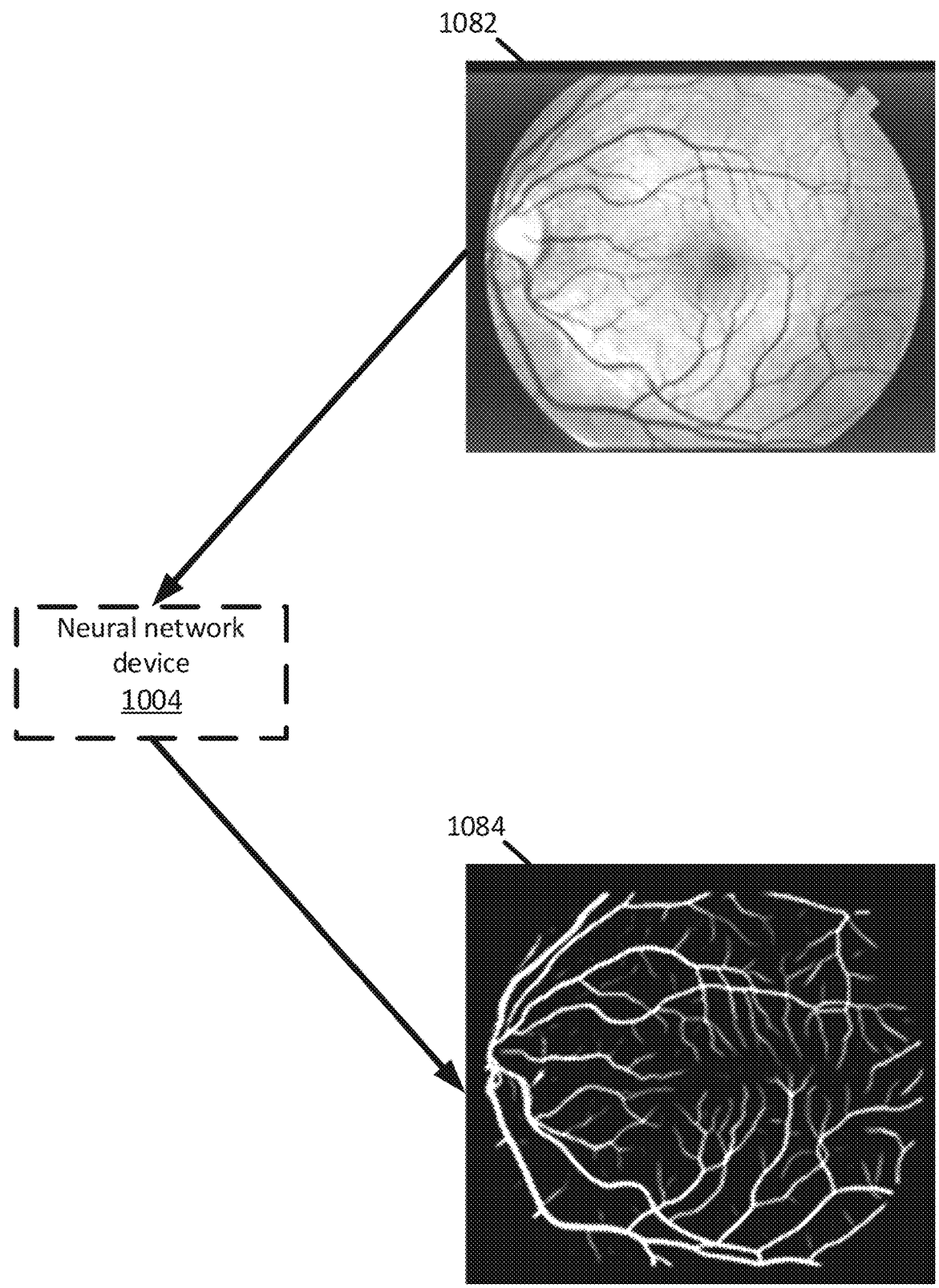
FIG. 22 is an example fundus image and corresponding vessel pixel image.

For example, referring to FIG. 22, an example fundus image 1082 is shown. The neural network device 1004 uses the trained models 1006, 1008, N to identify the vessels depicted in the image to estimate all vessel pixels, as illustrated in vessel pixel image 1084. This can be accomplished by implementing a U-net. Training samples are image masks with all vessel pixels being annotated. The U-net is then trained to learn vessel pixels and non-vessel pixels.

For images with little vessel count, indicating low quality or pathology (such as Frosted Branch Vascuopathy), then all regions are scanned to locate the OD and macula where fovea position can be estimated.

Referring again to FIG. 21, at operation 1058, the optical quality in the OD region can be classified using the trained models 1006, 1008, N. For example, human-annotated training samples can be used to create a customized CNN to automate the identification of quality in the OD. Vessel count in OD region can also be applied to determine its quality.

Next, at operation 1060, the vessel count for a particular region is estimated. This can be, for example, a measured vessel count for a region like a 1 disk diameter region or a 2 disk diameter region from the fovea or from the edge of the images. This can be accomplished using a combination of sub-window-based vessel count and field position based vessel count as shown below.

Figure 23:
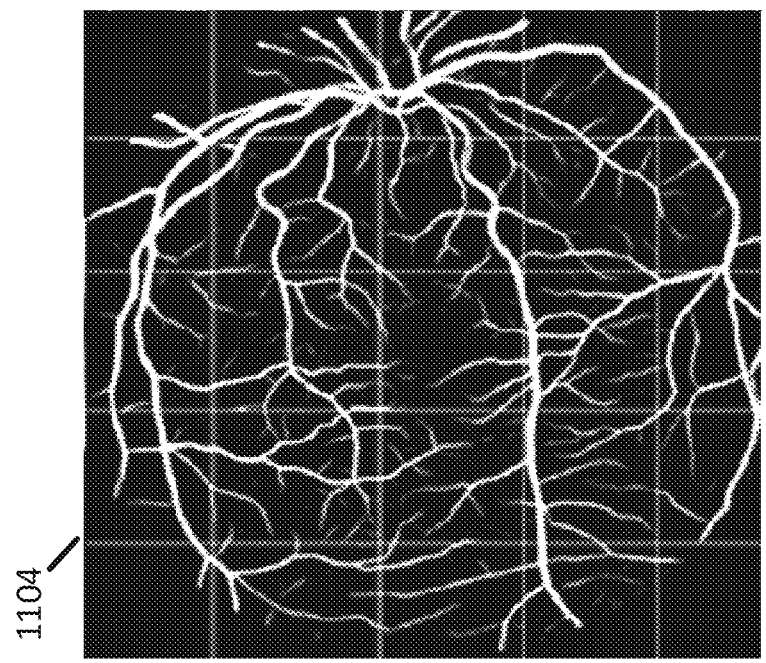
FIG. 23 is another example fundus image and corresponding vessel pixel image.
Figure 23:
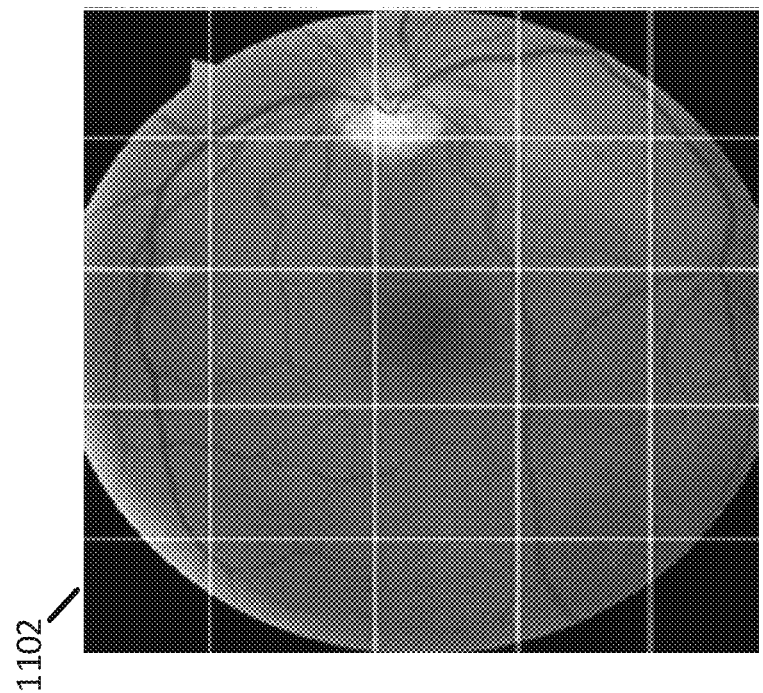
Figure 24:
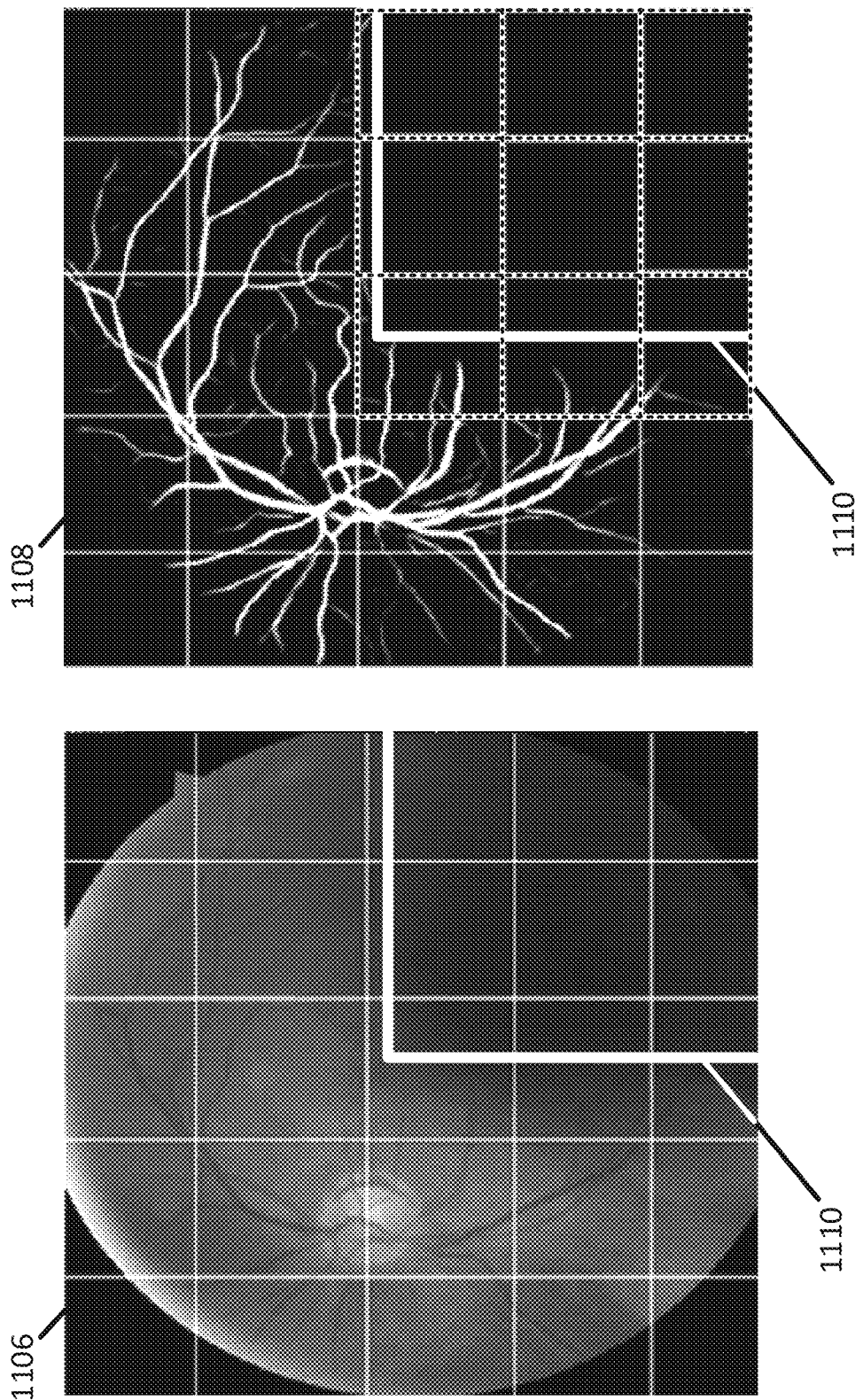
FIG. 24 is another example fundus image and corresponding vessel pixel image.

For example, as depicted at FIG. 23, a fundus image 1102 is analyzed by the neural network device 1004. The resulting vessel pixel image 1104 illustrates a good quality image having a high quality assessment score (e.g., 100). In contrast, at FIG. 24, a fundus image 1106 is analyzed by the neural network device 1004. The resulting vessel pixel image 1108 has fair quality image having a lower quality assessment score (e.g., 55) because of the lack of vessels within the region 1110.

In addition, the neural network device 1004 can be programmed to analyze the vessel count in the OD, macula regions. These can be assessed using, for example, the vessel counts as established in "Definition of acceptable image quality According to NHS National Screening Programme for Diabetic Retinopathy."

Figure 25:
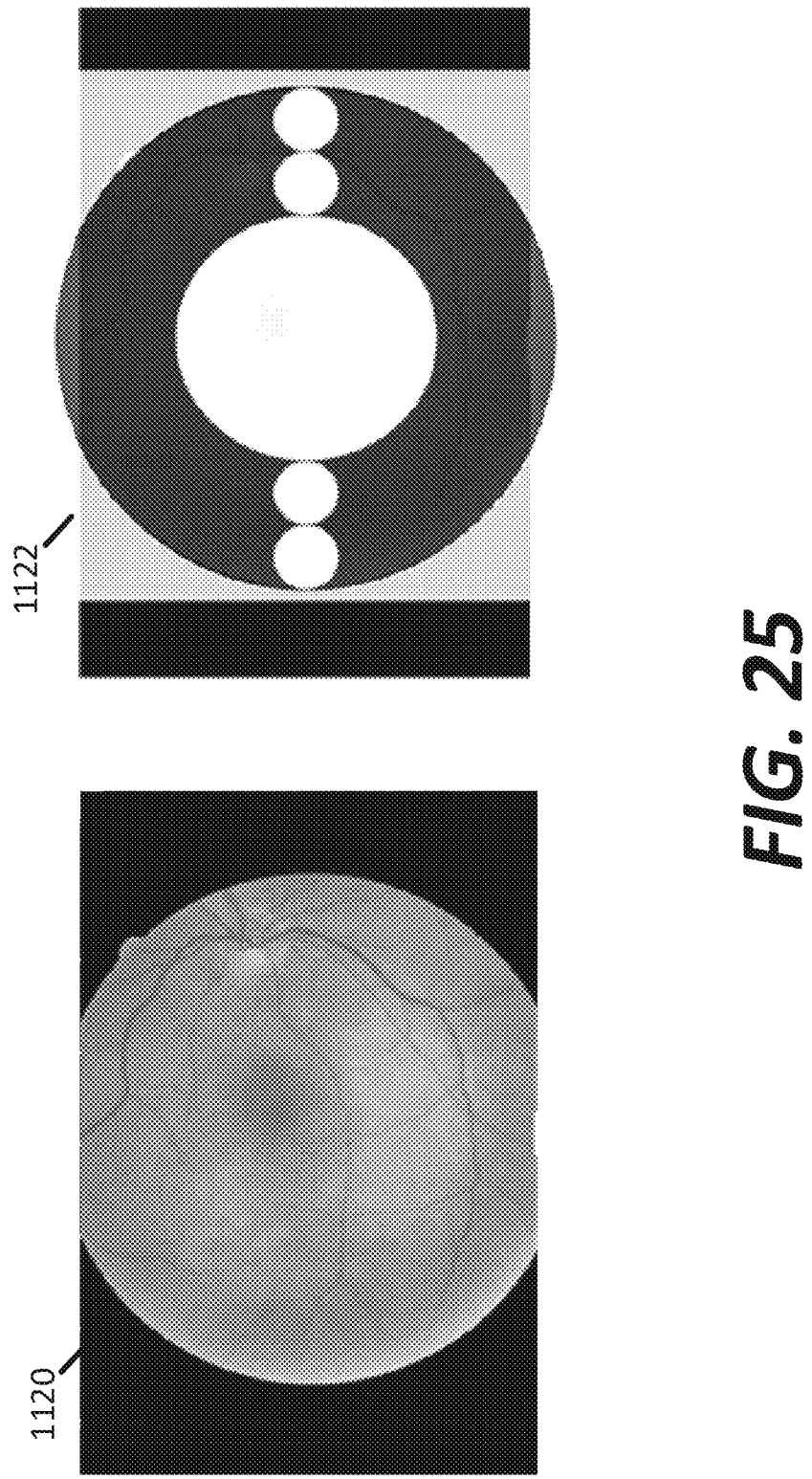
FIG. 25 is another example fundus image and mask applied thereto.

Referring again to FIG. 21, at operation 1062, the field position and classification of the fundus image (e.g., macular centered or OD centered) is determined. As depicted in FIG. 25, field position can be determined by applying a mask 1122 to the fundus image 1120, along with the use of macula and OD detection.

Referring again to FIG. 21, at operation 1064, feedback is provided by the neural network device 1004 to allow for the assessment of alternative disease states. For example, when the neural network device 1004 identifies an image of poor quality, other algorithms that detect pathologies can be used on the image, due to fact that certain pathological conditions prevent quality image to be taken (e.g., retinal detachments or severe PDR). Simple additional classifier-like logistic linear regression can be trained to combine the output from the image assessment module 1010 and the additional disease classifier to output an overall decision about the image condition (pure poor quality, or presence of referable pathology).

Finally, at operation 1066, a base line of one or more previous images can be used to focus analysis in a same region by comparing the previous images from the patient P—especially when there have been pathology signs present in baseline images. In some examples, the neural network device 1004 is programmed to identify a specific eye (e.g., right or left) so that images from that eye can be compared to baseline images. This can be accomplished through a comparison or registration of the vessel structures in two images, as well as the OD and macula locations. Locations where lesions have been detected from a baseline image can be examined to check the assessment and disease detection using relevant classifiers.

The specific order of the operations of the method 1050 can be modified and operations added or removed therefrom. For example, in an alternative method, the baseline comparison can be completed before any disease state analysis. Other configurations are possible.

The systems and method described herein result in a significant technical advantage. For example, the computing devices can be programmed to more efficiently analyze and classify fundus images. This allows the computing devices to accomplish an analysis of a greater number of images in a smaller amount of time.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A method for automating a quality assessment of digital fundus image, the method comprising:
    obtaining a digital fundus image file;
    analyzing a first quality of the digital fundus image file using a model to estimate an optimal time to capture a fundus image, wherein the optimal time is estimated dependent on a size of a pupil;
    capture a subsequent digital fundus image at the optimal time; and
    analyzing a second quality of the subsequent digital fundus image file using the model to estimate a disease state.

2. The method of claim 1, further comprising using a neural network to analyze the digital fundus image file.

3. The method of claim 2, further comprising embedding the neural network in an imaging device used to obtain the digital fundus image file.

4. The method of claim 1, further comprising analyzing an overall optical quality of the digital fundus image file as the first quality of the digital fundus image file.

5. The method of claim 1, further comprising analyzing the second quality of the subsequent digital fundus image file by determining whether the digital fundus image file depicts a retina.

6. The method of claim 5, further comprising detecting a fovea and an optic disc region in the subsequent digital fundus image file.

7. The method of claim 6, further comprising one or more of:
    determining an optical quality in the optic disc region;

determining a vessel count for a specified region of the retina;

determining a field position and classification of the subsequent digital fundus image file; and providing feedback to allow for assessment of alternative disease states.

8. A method for automating a quality assessment of digital fundus image, the method comprising:

obtaining a digital fundus image file;

analyzing an optical quality of the digital fundus image file using a neural network to estimate an optimal time to capture a fundus image, wherein the optimal time is estimated dependent on a size of a pupil;

capture a subsequent digital fundus image at the optimal time; and analyzing a second quality of the subsequent digital fundus image file using the model to estimate a disease state.

9. The method of claim 8, further comprising embedding the neural network in an imaging device used to obtain the digital fundus image file.

10. The method of claim 8, further comprising analyzing an overall optical quality of the digital fundus image file as the first quality of the digital fundus image file.

11. The method of claim 8, further comprising analyzing the second quality of the subsequent digital fundus image file by determining whether the digital fundus image file depicts a retina.

12. The method of claim 11, further comprising detecting a fovea and an optic disc region in the subsequent digital fundus image file.

13. The method of claim 12, further comprising one or more of:

determining an optical quality in the optic disc region;

determining a vessel count for a specified region of the retina;

determining a field position and classification of the subsequent digital fundus image file; and providing feedback to allow for assessment of alternative disease states.

14. A system for automating a quality assessment of digital fundus image, the system comprising:

a processor; and memory encoding instructions which, when executed by the processor, cause the system to:

obtain a digital fundus image file;

analyze an optical quality of the digital fundus image file using a neural network to estimate an optimal time to capture a fundus image, wherein the optimal time is estimated dependent on a size of a pupil;

capture a subsequent digital fundus image at the optimal time; and analyze a second quality of the subsequent digital fundus image file using the model to estimate a disease state.

15. The system of claim 14, wherein the neural network is embedded in an imaging device used to obtain the digital fundus image file.

16. The system of claim 14, wherein the memory encodes further instructions which, when executed by the processor, cause the system to analyze an overall optical quality of the digital fundus image file as the first quality of the digital fundus image file.

17. The system of claim 14, wherein the memory encodes further instructions which, when executed by the processor, cause the system to analyze the second quality of the subsequent digital fundus image file by determining whether the digital fundus image file depicts a retina.

18. The system of claim 17, wherein the memory encodes further instructions which, when executed by the processor, cause the system to detect a fovea and an optic disc region in the subsequent digital fundus image file.

19. The system of claim 18, wherein the memory encodes further instructions which, when executed by the processor, cause the system to perform one or more of:

determine an optical quality in the optic disc region;

determine a vessel count for a specified region of the retina;

determine a field position and classification of the subsequent digital fundus image file; and provide feedback to allow for assessment of alternative disease states.

20. The system of claim 14, wherein the memory encodes further instructions which, when executed by the processor, cause the system to use a base line of one or more previous images to focus analysis on the digital fundus image file.

* * * * *